United States Patent [19]
Keefe

[11] Patent Number: 5,792,072
[45] Date of Patent: *Aug. 11, 1998

[54] SYSTEM AND METHOD FOR MEASURING ACOUSTIC REFLECTANCE

[75] Inventor: Douglas H. Keefe, Omaha, Nebr.

[73] Assignee: University of Washington, Seattle, Wash.

[*] Notice: The term of this patent shall not extend beyond the expiration date of Pat. No. 5,594,174.

[21] Appl. No.: 630,004

[22] Filed: Apr. 8, 1996

Related U.S. Application Data

[63] Continuation-in-part of Ser. No. 567,999, Dec. 6, 1995, abandoned, which is a continuation-in-part of Ser. No. 254,311, Jun. 6, 1994, abandoned.

[51] Int. Cl.$^6$ ............................ A61B 5/12; G01H 15/00
[52] U.S. Cl. ................................... 600/559; 73/585
[58] Field of Search .......................... 128/746; 73/585, 73/587, 589; 600/559

[56] References Cited

U.S. PATENT DOCUMENTS

| | | | |
|---|---|---|---|
| 4,079,198 | 3/1978 | Bennett | 179/1 |
| 4,289,143 | 9/1981 | Canavesio et al. | 128/746 |
| 4,374,526 | 2/1983 | Kemp | 128/746 |
| 4,459,996 | 7/1984 | Teele | 128/746 |
| 4,601,295 | 7/1986 | Teele | 128/746 |
| 4,809,708 | 3/1989 | Geisler et al. | 128/746 |
| 4,884,447 | 12/1989 | Kemp et al. | 73/585 |
| 5,063,946 | 11/1991 | Wada | 128/746 |
| 5,105,822 | 4/1992 | Stevens et al. | 128/746 |
| 5,594,174 | 1/1997 | Keefe | 128/746 X |
| 5,651,371 | 7/1997 | Keefe | 128/746 |

FOREIGN PATENT DOCUMENTS

WO 95/33405   12/1995   WIPO.

OTHER PUBLICATIONS

P. Bray, "Click evoked otoacoustic emissions and the development of a clinical otoacoustic hearing test instrument," doctoral dissertation, University of London, London, England, 1989.

(List continued on next page.)

*Primary Examiner*—Francis Jaworski
*Attorney, Agent, or Firm*—Seed and Berry LLP

[57] ABSTRACT

A system and method of measuring the linear and nonlinear power-based responses of the ear uses a small probe assembly containing a sound source and microphone inserted into the ear. The linear power-based responses, or transfer functions, measured by the system include reflectance, admittance and impedance calculated in the time and frequency domains. A calibration procedure is based upon measured pressure responses in one or more calibration waveguides, and upon a model of the transfer function of each of the calibration waveguides that incorporates viscothermal losses. The linear transfer functions and the measured pressure responses in the ear may be combined to calculate sound power absorbed by the ear. The system is further able to measure the corresponding nonlinear power-based response of the ear by measuring any of the above transfer functions at different levels of the acoustic stimulus. These are used to calculate the nonlinear power absorbed by the ear when combined with the measured pressure responses in the ear at each stimulus level. A differential nonlinear transfer function of the ear and differential power absorbed by the ear are calculated based upon the level-dependent measurements of the transfer functions and the absorbed power. By delivering changes in static pressure applied to the ear via an additional probe tube in the probe assembly, the system is able to measure the dependence on static pressure of any of these linear and nonlinear power-based functions. The system is particularly useful in testing the auditory response of the human ear, with applications to the detection and diagnosis of abnormalities in the external, middle and inner ear of humans ranging in age from neonates to adults, as well as to the better understanding of the threshold audibility function in normal and hearing-impaired humans.

116 Claims, 8 Drawing Sheets

OTHER PUBLICATIONS

I. Blood et al., "Acoustic Otoscopic Measures in Toddler Population," Poster presented at the American Speech Language Hearing Association, Seattle, Washington, Nov., 1990.

D. Keefe et al., "Method to measure acoustic impedance and reflection coefficient," *J. Acoust. Soc. Am.* 91(1): 470–485, 1992.

D. Jurzitza and W. Hemmert, "Quantitative Measurements of Simultaneous Evoked Otoacoustic Emissions," *Acustica*, 77:93–99, 1992.

M. Joswig, "Impulse Response Measurement of Individual Ear Canals and Impedances at the Eardrum in Man," *Acustica* 77:270–282, 1993.

C. Shera and G. Zweig, "Noninvasive measurement of the cochlear traveling–wave ratio," *J. Acoust. Soc. Am.* 93(6):3333–3352, 1993.

D. Keefe et al., "Ear–canal impedance and reflection coefficient in human infants and adults," *J. Acoust. Soc. Am.* 94(5):2617–2638, 1993.

P. Dallos, "On the Generation of Odd–Fractional Subharmonics," *J. Acoust. Soc. Am.*, 40:1381–1391, 1966.

P. Dallos, *The Auditory Periphery*, Academic Press, U.S.A., 1973, pp. 448–464.

J. P. Wilson and J. R. Johnstone, "Basilar membrane and middle–ear vibration in guinea pig measured by capacitive probe," *J. Acoust. Soc. Am.*, 57:705–723, 1975.

D. T. Kemp and R. A. Chum, "Observations on the generator mechanism of stimulus frequency acoustic emissions –two tone suppression." In E. deBoer and M. A. Viergever (eds.), *Psycho–physical, Physiological and Behavioral Studies in Hearing*, Delft Univ. Press, pp. 34–41, 1980.

P. Dallos. Comment on "Observations on the generator mechanism of stimulus frequency acoustic emissions –two tone suppression." (D.T. Kemp and R. Chum). In E. deBoer and M. A. Viergever (eds.), *Psycho–physical, Physiological and Behavioral Studies in Hearing*, Delft Univ. Press, p. 42, 1980.

P. M. Zurek. "Acoustic emissions from the ear: A summary of results from humans and animals," *J. Acoust. Soc. Am.*, 78:340–344, 1985.

Voss, S. and J. Allen, "Measurement of Acoustic Impedance and Reflectance in the Human Ear Canal," *The Journal of the Acoustical Society of America* 95 (1), Jan. 1994 pp. 372–384.

Stevens, K. et al. "Calibration of Ear Canals for Audiometry at High Frequencies," *The Journal of the Acoustical Society of America* 81 (2), Feb. 1987, pp. 470–484.

Rabinowitz, W., "Measure of the Acoustic Input Immittance of the Human Ear," *The Journal of the Acoustical Society of America* 70 (4), Oct. 1981, pp. 1025–1035.

SYSTEM AND METHOD FOR MEASURING ACOUSTIC REFLECTANCE

CROSS-REFERENCE TO PRIOR APPLICATION

This application is a continuation-in-part of U.S. patent application Ser. No. 08/567,999, filed Dec. 6, 1995 now abandoned, which is a continuation-in-part of U.S. patent application Ser. No. 08/254,311, filed Jun. 6, 1994, now abandoned.

TECHNICAL FIELD

The system relates generally to a system and method for measuring acoustic reflectance, and more particularly, to a system and method for measuring the linear and nonlinear acoustic reflectance of the ear.

BACKGROUND OF THE INVENTION

Many hearing disorders are based upon abnormal states of the external, middle or inner ear. Quantitative data can be obtained by utilizing acoustic signals and responses measured in the ear canal. This data can be combined with other measurements to provide information used in the detection and diagnosis of hearing disorders, and the clinical management of existing hearing disorders.

One of the most basic acoustic tests has to do with the characterization of the linear response of the ear, assessed by measurements of such related responses as impedance, reflectance, reflectometry, impulse response and/or reflection function. The standard clinical impedance test is based upon tympanometry, which measures the acoustic admittance at a single frequency, or at a discrete range of frequencies. Tympanometry was developed for use in adults, and it is widely held that it is grossly inaccurate in testing neonates. One of the contributing factors is that tympanometry is dependent upon static pressurization of the ear canal, and this static pressure produces artifacts that are particularly troublesome in infants. Nonetheless, the clinical importance of measuring the linear response of the ear is well documented.

It is understood by those skilled in the art that the term linear response is an approximation to the actual response of the ear. It is further understood that the ear-canal responses to sound stimuli behave nearly linearly over a broad range of stimulus levels. The first-order description of the response of the ear typically utilizes a moderate-level stimulus and obtains the corresponding "iso-level function," which is ordinarily understood as the "linear response" of the system as an approximation to the idealized case. If a plurality of stimulus levels are used, there exist well-known techniques for estimating the linear-response component of the ear, even in the presence of nonlinearities. Except where otherwise noted, the term "linear response" is interpreted as the "transfer function or iso-level response" in a stimulus range where the nonlinear response of the ear is small in relative terms.

The second-order description of the response of the ear uses a plurality of stimulus levels to represent the nonlinear response of the ear. It is well known that the human ear reflects sound pressure at very long latencies, up to 40 milliseconds (ms) or more, after the presentation of an acoustic stimulus in the ear canal. At moderate stimulus levels, these nonlinear pressure responses are less than 3% or so of the total iso-level response. It is unknown to what extent these so-called evoked otoacoustic emissions distortion-product emissions represent a delayed reflection of the acoustic energy in the original stimulus (i.e., a passive model) or represent energy output from sites of power generation within the inner ear (i.e., an active-source model). This second-order description of the ear response is quantified in terms of a "nonlinear transfer function" of the ear, which is a plurality of "transfer functions," each measured at a particular stimulus level.

At present there is no convenient technique available to measure in a substantively simultaneous manner the linear and nonlinear responses of the ear which can be used to diagnose clinical abnormalities in the ear and differentiate between cochlear and conductive impairments. Therefore, it can be appreciated that there is a significant need for an instrument to characterize the linear and nonlinear responses of the ear. This and other advantages of the present invention will be apparent from the following detailed description taken in conjunction with the figures.

SUMMARY OF THE INVENTION

The present invention is embodied in a system for the measurement of a response of an ear for the measurement of the acoustic response of the ear. The system is comprised of a probe assembly positionable in proximity with the ear, an acoustic source within the probe assembly to produce an acoustic stimulus and deliver the acoustic stimulus to the ear in response to an electrical input signal, and an acoustical energy detector within the probe assembly to detect acoustic energy signals and to convert the detected acoustical energy signals to detected electrical signals. A stimulus generator produces an electrical input signal that is coupled to the acoustic source which outputs the acoustic stimulus.

The system includes one or more acoustic calibration waveguides, each having known acoustic transfer characteristics, predetermined dimensions and first and second ends, with the first end being opened. During a calibration period, the stimulus generator generates an electrical input signal when the probe assembly is positioned in the first end of an acoustic calibration waveguide. The resulting acoustic stimulus travels from the acoustic source to an acoustic boundary of the acoustic calibration waveguide such as the second end of the acoustic calibration waveguide, is reflected from the acoustic boundary, and travels back to the acoustic energy detector. A signal processor receives and processes the detected electrical signals.

In one class of embodiments, the electrical input signal has a known deterministic structure that enables separability of the incident waveform from any of the first-reflected or multiply-reflected waveforms in the acoustic calibration waveguide. From this separability, the system can be calibrated, at each stimulus level desired, to perform response function measurements in the ear for one or more stimulus levels. In the simplest embodiment, the duration of the electrical input signal is selected to be extremely short and the impulse response of the acoustic source is also assumed to be sufficiently short. The result is that the duration of the acoustic stimulus in the incident wave traveling away from the probe assembly has a duration less than a propagation time required for the acoustic stimulus to travel from the acoustic source to the closed end of an acoustic calibration waveguide, be reflected from the closed end, and travel back to the acoustic energy detector. In another embodiment, the electrical input signal has a duration that may be long compared to the round-trip propagation delay in the calibration waveguide, but this time-stretched electrical input signal is created using a known invertible function that takes as input a short-duration signal.

The inverse of this function is applied to the detected electrical signal from the acoustic energy detector in order to time-compress the detected electrical signal. While this time-compressed signal no longer has the fine structure of the acoustic waveform in the calibration waveguide, it enables separability of incident and reflected responses, and, thus, calibration of the response measurement system. Different embodiments based upon this condition of separability utilize one calibration waveguide or a plurality of waveguides.

After calibration is completed, the probe assembly is positioned in proximity with the ear to provide a substantially leak-proof seal. The electrical input signal is presented and the signal processor receives and processes the detected electrical signals to determine a transfer characteristic of the ear.

In one embodiment, each acoustic calibration waveguide is a cylindrical tube whose open end is substantially sealed by the probe assembly. However, the only requirement for the one or more acoustic calibration waveguides is that they be terminated by an acoustic termination having known acoustic transfer characteristics to define the calibration waveguide model. The calibration waveguides may have a cross-sectional area that varies as a function of position along the acoustic waveguide. For example, the calibration waveguide may be a cylindrical tube whose cross-sectional area is constant as a function of the position along the acoustic calibration waveguide. The second end of the one or more acoustic calibration waveguides may be a closed end or an open end. The system may also advantageously include storage means for storing the electrical input signal for use during the calibration and measurement periods. The system may also store data corresponding to the transfer characteristic of the acoustic source and acoustic energy detector for use during the measurement period to determine the transfer characteristic of the ear. The transfer characteristic of the ear may include the determination of any linear response function discussed above, for example, the reflectance.

In a preferred embodiment, at least one of the acoustic calibration waveguides has sufficient delay to separate the reflected and incident signals, and thus should be at least 25 centimeters (cm) in length, but it is convenient to choose it to be approximately 2 meters (m) in length.

Four different reflectance measurement techniques are disclosed to measure the linear response of the ear. In two of the measurement techniques only a single acoustic calibration waveguide is required. In the first technique, the incident signal must be separable from a first reflected signal. The computer processor determines the linear response function of the ear using the incident signal and only a first reflected signal as the set of detected calibration electrical signals. In this embodiment, the length of the acoustic calibration waveguide may be considered as having an effective length, based on such factors as the depth of insertion of the probe assembly into the acoustic calibration waveguide. The system can determine the effective length of the acoustic calibration waveguide by reiteratively calculating a value for the acoustic transfer characteristic of the acoustic calibration waveguide as a function of the effective length to minimize the difference between the acoustic transfer characteristic value and an acoustic transfer characteristic model value. Alternatively, the set of detected calibration electrical signals may contain the incident signal and a plurality of reflected signals, with the incident signal being separable from a first reflected signal. In this embodiment, the computer processor determines the linear response function using the incident signal and the plurality of reflected signals as the set of detected calibration electrical signals.

The remaining two reflectance measurement techniques use multiple acoustic calibration waveguides. In one embodiment, the system detects an incident signal that is separable from a first reflected signal in at least one of the plurality of acoustic calibration waveguides. The computer processor determines the linear response function of the ear based on a weighted average of the set of detected calibration electrical signals from the plurality of acoustic calibration waveguides, the detected measurement electrical signal, and the calibration waveguide model. The weighted average of the set of detected calibration electrical signals may be an equal weighted average. Alternatively, the computer processor may generate a prediction model for each of the plurality of acoustic calibration waveguides based on the calibration waveguide model for each of the acoustic calibration waveguides. In this embodiment, the weighted average is proportional to a function of the prediction model for each of the plurality of acoustic calibration waveguides. Another weighting function is proportional to a function of the set of detected calibration electrical signals from the plurality of acoustic calibration waveguides. As yet another alternative, the weighting may be proportional to a function of the prediction model for each of the plurality of acoustic calibration waveguides and a function of the set of detected calibration electrical signals from the plurality of acoustic calibration waveguides. This embodiment may use the incident and first reflected signal only as the set of detected calibration electrical signals from the at least one acoustic calibration waveguide. Alternatively, the system may use the incident signal and a plurality of reflected signals as the set of detected calibration electrical signals in the at least one acoustic calibration waveguide. The system may also use a reiterative process to determine an effective length for the plurality of acoustic calibration waveguides.

The fourth reflectance measurement technique does not require separability of the incident signal and first reflected signal. Instead, this technique relies on accurate estimates of the measurement system transfer characteristics based on an overdetermined system. Two measurement assisted characteristics must be determined to accurately define the measurement system transfer characteristics. In this embodiment at least three acoustic calibration waveguides are used. The measurement system parameters can be determined using an overdetermined set of matrix equation containing matrix elements that are functions of the set of detected calibration electrical signals when the probe assembly is positioned in each of the acoustic calibration waveguides, a prediction model of a predicted linear response for each of the acoustic calibration waveguides based on the calibration waveguide model for each of the acoustic calibration waveguides, and a weighted average of functions of the set of detected calibration electrical signals from the acoustic calibration waveguides. The computer processor determines the linear response function of the ear using detected measurement electrical signals and the measurement system parameters. The weighted average may be an equal weighted average, a weighted average proportional to a function of the prediction model for the at least three acoustic calibration waveguides, a weighted average proportional to a function of the set of detected calibration electrical signals for the at least three acoustic calibration waveguides, or a combination thereof. As with other measurement techniques, the system may determine an effective length through a reiterative calculation process.

The system may also include a pump to control the static pressure and thus permit the measurement system to determine the linear response as a function of static pressure within the one or more acoustic calibration waveguides, and within the ear. An estimate of the area of the ear canal can be provided to the computer processor along with a response function of the ear as a function of static pressure. The computer processor determines a linear response function of the ear as a function of static pressure. In one embodiment, the pump and signal processor are portions of a conventional tympanometer. The tympanometer determines a function such as admittance as a function of static pressure. The computer processor receives the admittance function data and the ear canal area estimate and determines a linear response function of the ear as a function of static pressure. The stimulus generator may also generate a signal at a selected frequency, with the signal processor calculating the response function of the ear as a function of the selected frequency. In this embodiment, the computer processor calculates the linear response function of the ear as a function of static pressure and frequency.

The system is also capable of measuring a nonlinear power-based transfer function of the ear. The system uses one or more acoustic calibration waveguides in the manner previously described. The stimulus generator generates the electrical input signal at first and second stimulus levels to cause the acoustic source to produce acoustic stimuli at first and second acoustic stimulus levels when the probe assembly is positioned in the ear. The computer processor determines a first power-based transfer function of the ear based on the set of detected calibration electrical signals, the detected measurement electrical signals in response to the acoustic stimulus at the first acoustic stimulus level, and the calibration waveguide model. The computer processor determines a second power-based transfer function of the ear based on the detected calibration electrical signals, the detected measurement signals in response to the acoustic stimulus at the second acoustic stimulus level, and the calibration waveguide model. The computer processor further determines the power-based nonlinear transfer function based on the first and second transfer functions. The power-based transfer functions may be determined by any of the four techniques previously described.

In one embodiment, the stimulus signal generator generates the electrical input signal at the first and second stimulus levels when the probe assembly is positioned in the first end of each of the one or more acoustic calibration waveguides. This permits the system to accurately determine the first power-based transfer function based on the set of detected calibration electrical signals at the first acoustic stimulus level, along with the measurement electrical signals at the first acoustic stimulus level, in the calibration waveguide model, while the second transfer function of the ear is based on the set of detected calibration electrical signals at the second stimulus level, the detected measurement electrical signals at the second acoustic stimulus level, and the calibration waveguide model. Alternatively, the stimulus signal generator may generate the electrical input at the first stimulus level only when the probe is positioned in the first end of the one or more acoustic calibration waveguides. In this case, the detected calibration electrical signals include signals detected in response to the acoustic stimulus at the first acoustic stimulus level.

DETAILED DESCRIPTION OF THE INVENTION

Figure 1:
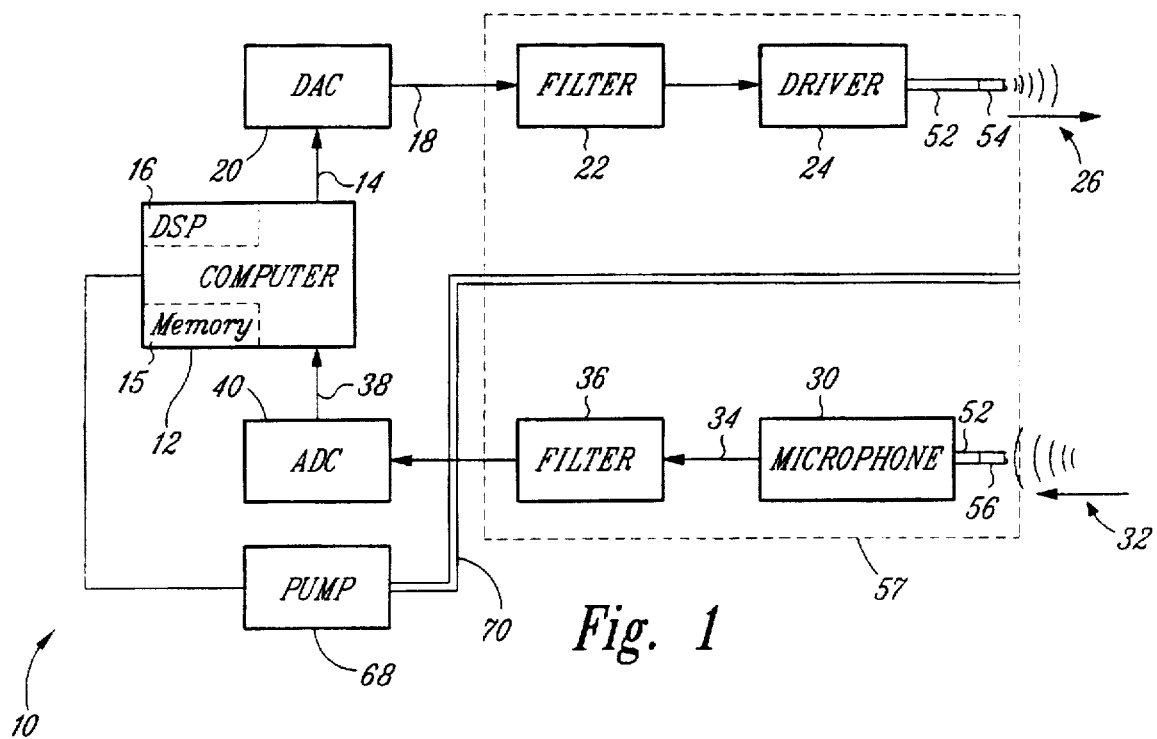
FIG. 1 is a functional block diagram of the system of the present invention.

The present system provides a novel technique for measuring the linear response of the ear, with or without manipulation of the static pressure in the ear canal, that provides data over most of the frequencies in the range of hearing, that is simple to use in infants or adults, and that is a rapid test. As will be discussed in detail below, the present invention provides a technique to determine the acoustical characteristics of the measurement system and thus account for the effects of the measurement system when performing tests in the ear. One technique used by the present invention to determine the acoustical characteristics of the measurement system relies on the principle of separability of an incident acoustic stimulus signal and a first reflected signal in a calibration phase of the system. Alternatively, multiple measurements can be used in an overdetermined system to estimate the acoustic characteristics of the measurement system. Finally, this system provides a means to extract meaningful estimates of power transfer when used in conjunction with otoacoustic emission measurements (OAE) known in the art. OAE measurements are valuable because they provide information on the state of the inner ear. An abnormal OAE measurement may be due to the state of the inner ear or middle ear, but the OAE technique cannot differentiate between these two possible sites of pathology. The present invention provides a means of detecting abnormalities in the middle and external ear. When used in conjunction with OAE, ABR or distortion product (DP) measurements, all techniques that are said to measure abnormalities in the inner ear or auditory neural pathway, the present invention provides a more refined clinical diagnosis concerning the site of the abnormality.

As previously discussed, the measurement systems of the prior art measure OAE or EOAE based upon pressure measurements in the ear canal. These prior art measurements do not provide information about power transmitted into the middle ear and inner ear, nor do they provide information about power received from the ear in the form of emissions. Power-based techniques of the present invention give a more fundamental description of the evoked response of the ear to sound stimuli. The present invention provides practical devices to measure the power transmitted by an acoustic stimulus into the ear-canal and the power received due to the presence of EOAEs. The present invention provides a substantial improvement of the EOAE measurement technique using the more fundamental domain of power measurements rather than pressure measurements of the prior art.

The system of the present invention can measure the linear and nonlinear acoustic reflectance of the ear, the combination of which is termed otoreflectance. This otoreflectance may be calculated in the frequency domain as the reflection coefficient and in the time domain as the reflection function, and other acoustic response functions such as impedance and impulse response are calculated from the reflectance using well known transformations. It allows dual measurements of the presence of a conductive impairment and the presence of a cochlear impairment, thereby giving more complete information on the state of the ear. There may be significant clinical applications in hearing for this device, not only for neonates for which the priority for early detection is so high, but also for adults including the elderly population with their specific types of hearing disorders.

There exist a number of linear response functions that may be applied to hearing measurements. Acoustic pressure is not such a linear response function, because the pressure response in a linear system varies with stimulus level. Linear response functions allow a power-based description of the acoustic response of the ear. This is not possible with pressure measurements alone. Linear response functions may be understood within an input-output system framework, as the ratio of an output response signal to an input excitation signal. This ratio is the transfer function of the input-output system. The sub-class of linear response functions is considered such that the stimulus and response are measured at the same location, as is the case for the ear-canal measurement systems within this application. Linear response functions may be classified into two broad categories, depending on whether the response function varies with time or frequency. Any time-domain linear response function can be interpreted as the system output in time when the stimulus is an idealized impulse, that is, a signal with flat power spectrum and very short duration. Any frequency-domain linear response function can be interpreted as the system output in frequency when the stimulus is sinusoidal with unit amplitude and zero phase.

Frequency-domain linear response functions include (acoustic) admittance, (acoustic) impedance, and the pressure reflection coefficient. All these functions are complex quantities of frequency. The admittance is the volume flow response at a given frequency to a unit pressure sinusoid at the same frequency. The impedance is the pressure response sinusoid to an input volume-flow sinusoid. Admittance and impedance are standing wave descriptions of the sound field whereas the (pressure) reflection coefficient is a traveling wave description. The pressure reflection coefficient is the ratio of two sinusoids: the reflected pressure wave and an outgoing pressure wave associated with the stimulus. Other frequency-domain linear response functions exist that can be expressed in terms of these functions.

Time-domain linear response functions include the impulse response and the reflection function. The impulse response is the pressure response as a function of time to a unit volume-flow impulse. It is formally related to the impedance by the inverse Fourier transform so that it is also called the time-domain impedance. Another response function that may be defined is the time-domain admittance which is the inverse Fourier transform of the admittance. The (pressure) reflection function is the reflected pressure response as a function of time to an out-going incident impulse of pressure. It is formally related to the pressure reflection coefficient by the inverse Fourier transform.

The term reflectance is used to refer to either the reflection coefficient in the frequency domain or reflection function in the time domain. There are also volume-flow reflectance that are related in well-known ways to the pressure reflectances.

Such linear response functions may be extended to the nonlinear regime by measurement of a plurality of responses at different stimulus levels. At each given stimulus level, the definition of a response function is identical to that of the corresponding linear response function, or iso-level transfer function. Thus, the system transfer function is measured as a function of stimulus level. Such nonlinear transfer functions include reflectance, admittance and impedance, each measured in the time or frequency domain at a plurality of stimulus levels. For example, one may measure the reflectance (in time or frequency domains) at various levels to obtain a nonlinear reflectance.

Both linear and nonlinear response functions can be measured at various levels of static pressure in the ear. For example, the admittance can be measured as a function of frequency and static pressure, and can be operationally defined in the linear, i.e., iso-level, regime as well as the nonlinear regime.

Although pairs of time-domain and frequency-domain linear-response functions are formally related by the Fourier transform and inverse Fourier transform, it is well known that a measurement of a frequency-domain response does not necessarily enable an accurate measurement of the corresponding time-domain response. For example, an accurate discrete-time measurement of the impedance cannot necessarily be used to calculate an accurate measurement of the impulse response by straightforward application of the inverse discrete Fourier transform. The reason is that the formal relationships in terms of the Fourier transform presume an infinite bandwidth and an absence of noise. Experimental measurements of, for example, the impedance are obtained over a finite bandwidth, and the response at frequencies outside the bandwidth is dominated by noise. It is well known that the inverse discrete Fourier transform mixes up the noise throughout the entire range of the corresponding time-domain response. Thus, the measurement of a frequency-domain response function is best obtained using a frequency-domain measurement, and the measurement of a time-domain response function is best obtained using a time-domain measurement (D. H. Keefe, R. Ling, and J. C. Bulen, "Method to Measure Acoustic Impedance and Reflection Coefficient," *J. Acoust. Soc. Am.* 91:470–485, 1992). This is also true for measurements in the nonlinear regime as the noise/finite bandwidth problems are embedded in measurements at each stimulus level.

One of the formal properties of a linear response function is that it is invariant with respect to changes in the temporal-spectral structure of the stimulus. This formal property also does not translate into real measurements of linear response functions. The influence of noise varies with the structure of the stimulus. It is advantageous to maximize the level of the signal relative to that of the noise, but there exists a tradeoff with nonlinearities in the measurement transducers, typically an acoustic source loudspeaker and microphone. A common problem in measurement transducers that limits the performance of measurement systems in hearing is the existence of peak-clipping nonlinearities. Thus, the signal level cannot be increased to an arbitrarily high level as peak-clipping in the transducer occurs. A solution is to manipulate the temporal-spectral structure of the stimulus so as to enhance the signal-to-noise ratio without overloading the measurement transducers, as in the time-stretched signals to be described.

The present invention is embodied in a system 10 shown in the functional block diagram of FIG. 1. A computer 12 generates a stimulus signal 14 used by the system 10. The computer 12 is a conventional device that may include memory 15 and a digital signal processor (DSP) 16 to generate the stimulus signal. The design of the stimulus signal 14 will be described in detail below. The stimulus signal 14 is converted to an analog signal 18 by a digital to analog converter (DAC) 20. The analog signal 18 can be filtered by a conventional lowpass filter 22 in a manner well known to those of ordinary skill in the art of signal processing. The output of the lowpass filter 22 is coupled to a driver 24 that transducers the electrical signal to an acoustic signal 26. It is the acoustic signal 26 that will be used to determine the linear and nonlinear responses of the ear.

The system 10 also includes a microphone 30 or other acoustic energy detector to detect a reflected acoustic signal 32 and transducers the reflected acoustic signal into a detected electrical signal 34. The acoustic energy detector may be a pressure transducer, piezoelectric transducer, or any other well-known device for transducing acoustic energy into electrical energy. The present invention is not limited by the specific form of the acoustic energy detector. The detected electrical signal 34 is filtered by a conventional lowpass filter 36 to eliminate aliasing effects and converted to a digital signal 38 by an analog to digital converter 40. The digital signal 38 is analyzed by software in the computer 12 and the DSP 16 to determine a pressure response to the stimulus signal. A conventional pump 68 coupled to the ear tip 58 of the probe assembly 50 by a tube 70 is used to control the static pressure. The system 10 determines the linear and nonlinear responses of the ear based on the pressure response of the microphone 30. Details of the signal analysis are provided below.

Figure 2:
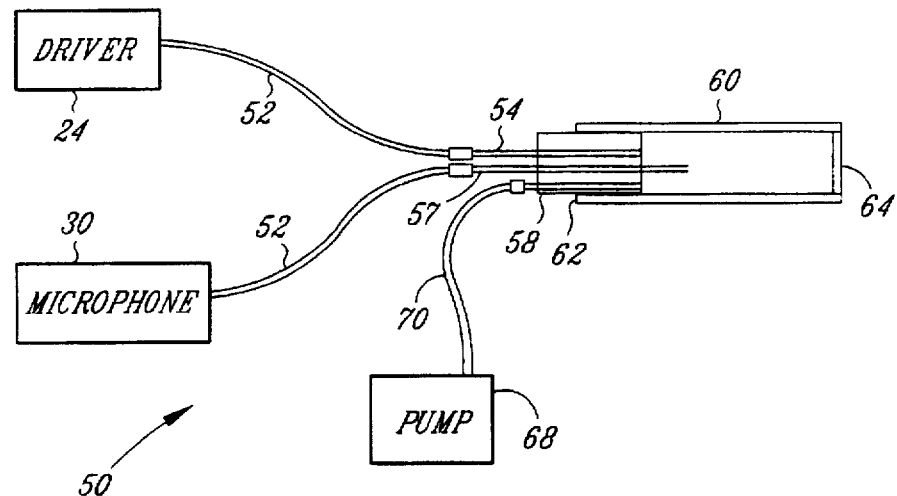
FIG. 2 is a side view of the probe assembly of the system of FIG. 1.

The driver 24 and microphone 30 are both included in a probe assembly 50, shown in FIG. 2. The driver 24 in the presently preferred embodiment of the system is an Etymotic ER-10C probe driver. The microphone 30 in the presently preferred embodiment of the system is a microphone included in the Etymotic ER-10C probe. The driver 24 and the microphone 30 are each coupled to the probe assembly 50 by small flexible tubes 52. The flexible tubes 52 are relatively short to minimize signal loss and thus maximize the signal-to-noise ratio (SNR) of the system 10. However, the precise length of the flexible tubes 52 is not critical because the system 10 will determine the acoustic transfer characteristics of the driver 24, microphone 30, filters 22 and 36, and the flexible tubes 52. The flexible tubes 52 couple the driver 24 and the microphone 30 to a driver probe 54 and a microphone probe 56, respectively, within the probe assembly 50. The probe assembly 50 includes a variety of standard eartips 58 fitted to accommodate the range of human ear-canal sizes from neonate to adult.

The operation of the system 10 is comprised of an optional stimulus generation phase, followed by the mandatory calibration and evaluation phases. In the stimulus generation phase, the system 10 uses a novel technique for generating a stimulus signal having the desired acoustical properties. Under normal use, the system 10 need only be derive the stimulus signal once at the time of assembly. The present invention also provides a novel technique for calibrating the system 10 during the calibration phase of operation. Generally, the user calibrates the system 10 for each patient. However, the system 10 provides a simple calibration procedure that easily permits such calibration. In the measurement phase of operation, the system 10 collects and analyzes data from the ear and determines therefrom information relating to the condition of the middle and inner ear. One aspect of the system 10 is its ability to measure the linear response of the ear in a manner that permits its use with existing nonlinear measures such as EOAE, DP and ABR techniques.

An iso-level response measurement system is said to be calibrated when the system can be used to measure the iso-level response of an unknown termination, for example, iso-level response of the ear. It is well known that frequency-domain measurements of the Thevenin impedance and Thevenin source pressure establish such a calibration, and that frequency-domain measurements of the Norton admittance and Norton source volume velocity also establish such a calibration. Because the inverse Fourier transform can be applied to transform the Thevenin or Norton circuit parameters into the time domain, it can readily be appreciated that a calibration procedure can be achieved by determination of the corresponding time-domain circuit parameters. In addition, this invention discloses an alternative reflectance circuit representation, in which calibration is achieve by measurement of an incident pressure signal and the reflectance of the probe assembly, and that such representations are possible in both time and frequency domains. No matter which circuit representation (Thevenin, Norton, reflectance) is chosen or which domain (time or frequency), calibration is achieved when two quantities in the circuit representation are calculated at each discrete step in time or frequency. One of these quantities is associated with the stimulus produced by the source, for example, the Thevenin source pressure, and the other of these quantities is associated with the acoustic discontinuity at the surface of the probe, for example, the Thevenin source impedance.

Probe Assembly Issues

The system 10 determines the linear response of the ear based upon the finding that the human external, middle and inner ear can be viewed as a one-dimensional acoustic waveguide. The linear acoustic response of the ear can be measured by placing the probe assembly 50 in the ear canal and conducting measurements using the system 10. The driver 24 produces a short-duration sound field (i.e., the acoustic signal 26). The microphone 30 measures the sound pressure and the system 10 derives a reflectance of the ear from the microphone response. The reflectance is used to measure the acoustic properties of the ear. In addition to the acoustic wave that propagates down the acoustic waveguide, the driver has a non-propagating mode. This non-propagating mode, sometimes called an evanescent mode, refers to acoustic signals that are non-propagating at sufficiently low frequencies such that the acoustic wavelength is small relative to the circumference of the flexible tubes 52 or ear canal. These evanescent modes describe the localized acoustic field near the probe assembly 50. Any localized, non-propagating acoustic field caused by evanescent modes in the vicinity of the probe assembly 50 can be attenuated by restricting the frequency content of the external stimulus or by other well-known methods such as drawing the microphone probe 56 slightly beyond the plane of the driver probe 54, as shown in FIG. 2. While the examples presented herein are directed to measurements of the auditory system, the principles of the present invention are applicable to any waveguide such as a musical instrument air column.

Stimulus Design Phase

As those skilled in the art can appreciate, there is some degree of variation in the acoustic and electrical response of the driver 24 and the microphone 30. For example, the frequency response of the driver 24 varies from one driver to another and will also vary depending on the acoustical impedance of the load to which the driver is coupled and may also be nonlinear. Proper operation of the system 10 requires the generation of an electrical stimulus signal that is custom designed for the specific driver 24 and the specific microphone 30 used for each system. The system 10 custom designs a stimulus signal that compensates for nonlinearities and variations in frequency response of the driver 24, microphone 30, flexible tubes 52, and associated signal conditioners such as amplifiers (not shown) and filters 22 and 36. These components are shown within the dashed line of FIG. 1 and will be referred to herein as a measurement subsystem 57. The stimulus generation procedures used by the system 10 can be applied to a stand-alone system, such as Auditory Brainstem Response (ABR) and EOAE systems. The stimulus generation procedures described herein are also needed as an initial step in the hearing assessment measurement performed by the system 10. As long as the probe assembly 50 performance is not seriously degraded such as by dropping or otherwise damaging the probe assembly, the stimulus design phase does not have to be carried out by the end-user of the system. Thus, the stimulus signal can be custom designed for the specific driver 24 and microphone 30 at the time of assembly and does not have to be repeated each time the system 10 is used. Nevertheless, the user can redesign a new stimulus, if desired.

The system 10 calculates the custom designed stimulus signal based upon measurements in a single calibration waveguide 60 or calibration tube whose cross-section area is similar to the ear-canal area in the human subject(s) to be tested, or the entryway area of any other unknown system. The length of the calibration waveguide 60 is typically between 25–350 centimeters (cm), however, the length of the calibration waveguide is not critical so long as it permits the separation of incident and reflected signals, as will be discussed below. The calibration waveguide 60 has an open first end 62 in which the probe assembly 50 is inserted and a second end 64 opposite the first end 62. The acoustical characteristics of the calibration waveguide 60 are derived from a model of a cylindrical tube, as will be described below. The calibration waveguide 60 is a straight hard-walled cylindrical tube with a circular cross-section, but a flexible-walled tube or coiled cylindrical tube can also be used. Those skilled in the art can appreciate that the calibration waveguide 60 can be an acoustic waveguide of virtually any shape, such as square tube, oval tube, conical tube or the like, whose cross-section as a function of position along the length of the calibration waveguide is known and whose acoustical properties, including viscothermal effects, can also be derived by modeling.

The calibration waveguide 60 in the preferred embodiment has an open first end 62 to permit the insertion of the probe assembly 50 and a closed second end 64 that reduces the effects of ambient noise and can be modeled very accurately. However, the calibration waveguide 60 may be virtually any shape or dimension and have a closed second end 64 or an open second end so long as the acoustical transfer characteristics of the calibration waveguide can be modeled. Furthermore, as will be discussed below, the incident and reflected signals may overlap acoustically if they are separable by signal processing.

Figure 3:
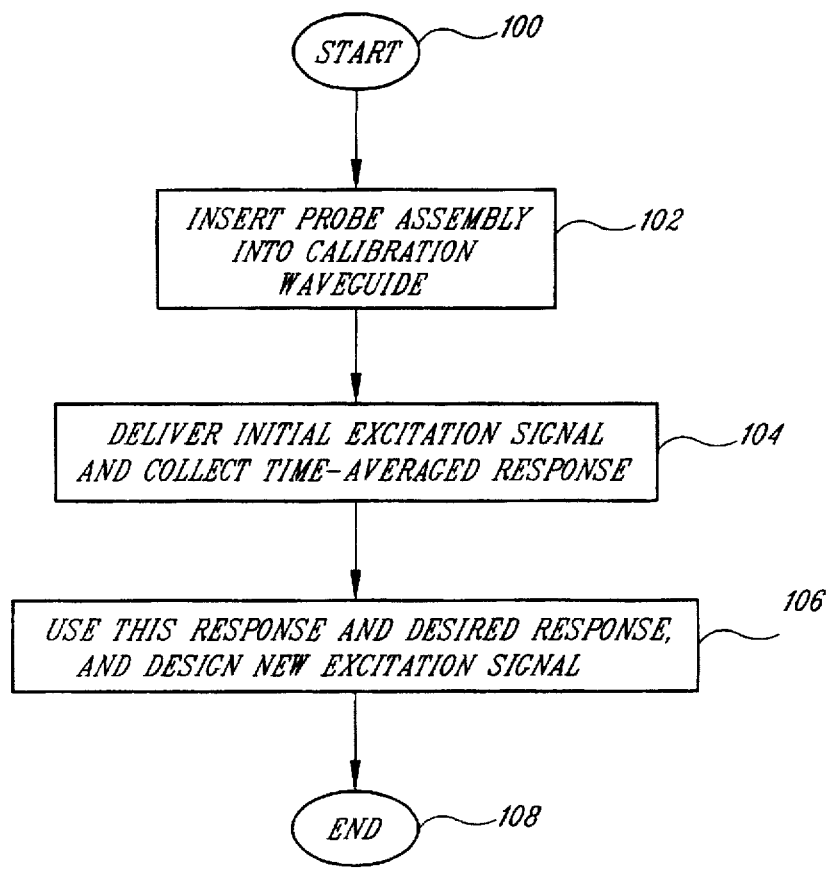
FIG. 3 is a flowchart of the stimulus design procedure used by the system of FIG. 1.

The stimulus generation procedures are described below in conjunction with the flowchart of FIG. 3. The system 10 starts at 100 with the probe assembly 50 (see FIG. 2) having unknown transfer characteristics. In step 102, the eartip 58 and the probe assembly 50 are inserted into the open end 62 of the calibration waveguide 60 and forms a substantially leak-proof seal of the open end. In the present embodiment, the probe assembly 50 is not vented to the ambient atmosphere. However, because the system 10 characterizes the transfer characteristics of the probe assembly 50 and other associated circuitry such as the filters 22 and 36, it automatically compensates for a well-defined pressure leak such as a vent tube. Leaks from the side of the eartip 58 are not well defined because they change from one insertion to another. These types of leaks should be avoided.

In step 104, the system 10 generates a short-duration electrical signal $e_s$ for the DAC 20 (see FIG. 1) and measure the pressure response $p_s$. The calibration waveguide 60 is chosen to be sufficiently long and the duration of the electrical signal $e_s$ is sufficiently short so that the initial pressure response is due only to the response of the driver 24 to the DAC signal, and is independent of sound reflections from the opposite closed end 64 of the calibration waveguide. The duration of the electrical signal $e_s$ is selected so that the output of the driver 24 has died away before the first reflection arrives at the probe assembly 50 from the closed end 64 of the calibration waveguide 60.

In step 106, the system 10 applies a signal processing algorithm, described below, that takes as input the electrical signal $e_s$, the pressure response $p_s$ and the desired incident pressure signal $p_i$ that the driver 24 should produce. For many types of hearing tests it is desired that the incident pressure signal $p_i$ generated in the ear canal in the absence of reflections from the eardrum should approximate an impulse with a finite frequency bandwidth. This describes a class of signals that in the digital domain can be designed using well-known finite impulse response (FIR) or infinite impulse response (IIR) techniques. Because these techniques are well known to those of ordinary skill in the art, they will not be described in detail herein.

Choosing a particular band-limited impulse as the desired incident pressure signal $p_i$, the system 10 uses the following signal processing algorithm to design an electrical stimulus signal $e_i$ that will cause the driver 24 to generate the desired incident pressure signal $p_i$. When the electrical stimulus signal $e_i$ is applied as input to the driver 24, the desired incident pressure signal $p_i$, or at least, a good approximation thereof, is produced as the acoustic signal 26 (see FIG. 1). This tends to reduce the influence of the frequency and phase responses of the driver 24 from subsequent processing, although the deconvolution step described below further reduces the influence of the measurement system, including the driver.

One can consider the special case where both electrical signal $e_s$ applied to the driver 24 and the desired incident pressure signal $p_i$ are equal to the impulse response d of a FIR lowpass filter, designed using the Park-McClelland method. To clarify whether a formula is in the time domain or the frequency domain, the time-domain formulas express the unknown as a function of time t, and the frequency-domain formulas express the unknown as a function of frequency $f$. The pressure response $p_s$ (t) is the convolution (denoted by the operator "*") of $e_s$ (t) with the impulse response h(t) of the measurement subsystem 57 and has the following form:

$$p_s(t)=h*e_s=h*d \quad (1)$$

It should be noted that mathematical relationships that are functions of time or frequency are designated by the argument "(t)" or "(f)," respectively on the left-hand side of equations. For the sake of clarity, those arguments are often omitted from the right-hand side of the equations. However, those skilled in the art will recognize that certain elements in the equations are functions of time or frequency based on the argument in the left-hand side of the equation, and on the presence or absence, respectively, of the convolution operator.

One can calculate the electrical signal $e_i$ producing the acoustic band-limited impulse $p_i$ via the convolution:

$$p_i(t)=d(t)=h*e_i. \tag{2}$$

It follows from equations (1) and (2) that $$p_s*e_i=d*d \tag{3}$$

in which $p_s$ is measured and $d$ is known. Equation (3) is solved for $e_i$ using deconvolution (DECONV) by well-known techniques such as Singular Value Decomposition (SVD), Conjugate Gradient method (CG), Neural Network Method, Fourier transform techniques, or the like. The solution is expressed as:

$$e_{i(t)}=\text{DECONV}(d*d, p_s). \tag{4}$$

It is this electrical stimulus signal $e_i$, applied to the DAC 20, that results in the band-limited impulse waveform $p_i=d$. The above example illustrates the calculation of the electrical stimulus signal $e_i$ using deconvolution in the time domain. However, the electrical stimulus signal $e_i$ may also be calculated by division in the frequency or Laplace domain. The main constraint is that the incident signal be separable from the reflected signal. The system 10 ends the stimulus generation procedure in step 108.

Before any meaningful measurement of the acoustic response in the ear canal can be measured, the system 10 must be calibrated. To be useful, a hearing assessment device must be simple enough to be operated by a clinically trained audiologist. Existing devices, such as a tympanometer, often rely on calibration within one or more cavities or resonators of known geometry. These devices are limited in the frequency range over which they can be used. In contrast, the system 10 is capable of accurate measurements over a broad range of frequencies up to 20 kilohertz (kHz) depending on the source and microphone characteristics and the influence of the higher-order acoustic modes that describe the localized acoustic field near the probe assembly 50.

Reflectance Technique I

In Reflectance Technique I the system 10 requires only one calibration waveguide 60 that is simple to use and is similar in function to calibration cavities that are already familiar to clinicians.

Figure 4:
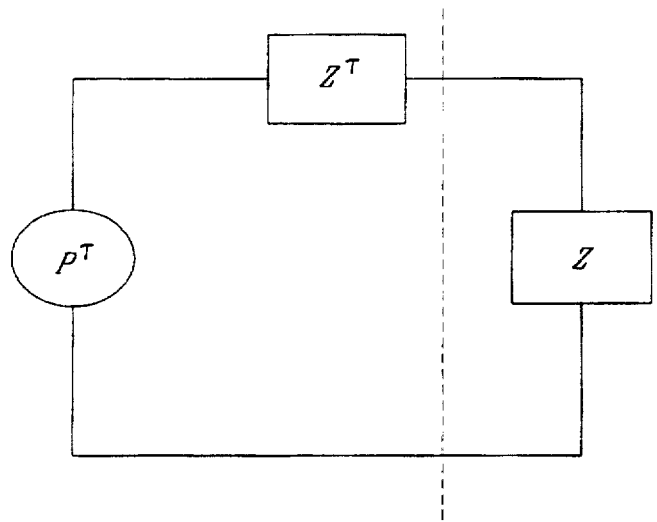
FIG. 4 is a Thevenin model of the probe assembly of the system of FIG. 1.

It is well known that the acoustic response of the measurement subsystem 57 can be represented in the frequency domain by the Thevenin equivalent pressure $P^T$ and Thevenin impedance $Z^T$. The Thevenin impedance is illustrated in FIG. 4 where the measurement subsystem 57 is characterized by the Thevenin pressure $P^T(f)$ and the Thevenin impedance $Z^T(f)$. An arbitrary load is characterized by the load impedance $Z(f)$ in FIG. 4. Once the Thevenin parameters of the measurement subsystem 57 are determined, it is possibly to apply the measurement subsystem to an unknown acoustic termination and measure its acoustic impedance. In the case of the human ear, the acoustic termination comprises the ear canal terminated by the eardrum, middle ear and inner ear.

These Thevenin parameters can be measured by means of a calibration procedure. For simplicity in understanding the present invention, the Thevenin description is employed to derive the relationships between incident and reflected pressure waves in the calibration and unknown waveguides, but the end result is independent of the Thevenin circuit parameters. This relationship is given below. A complementary representation of the Thevenin parameters is also possible in the time domain by a systematic replacement of the multiplication of transforms in the frequency domain by convolution of signals in the time domain. It is well known that this can be equally well represented by a Norton equivalent circuit.

Figure 5:
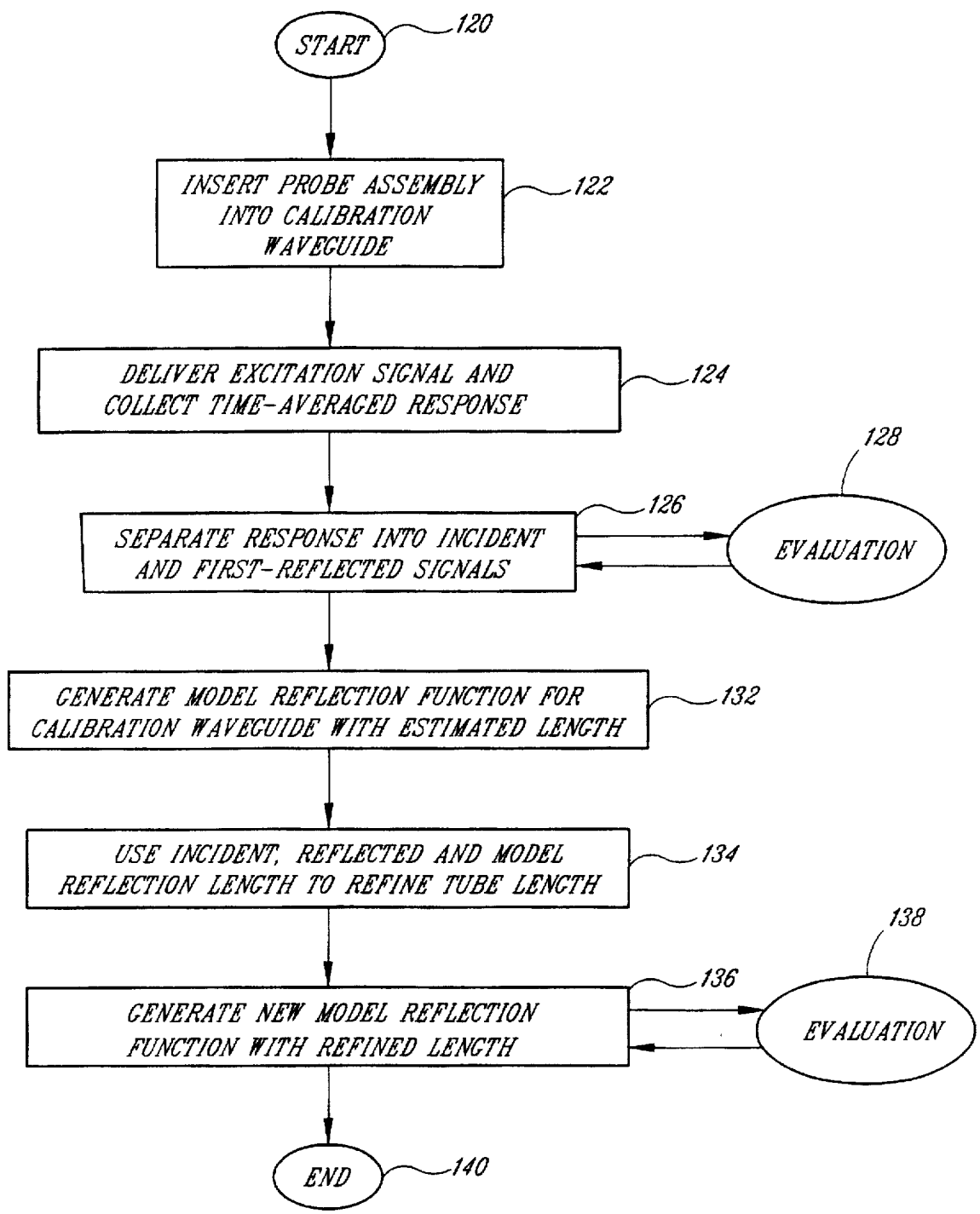
FIG. 5 is a flowchart of the calibration procedure used by the system of FIG. 1 with a single acoustic calibration waveguide.

The calibration procedure is given below in conjunction with the flow chart of FIG. 5. The user starts in step 120 with the uncalibrated probe assembly 50 (see FIG. 2). In step 122 the user inserts the probe assembly 50 and eartip 58 into the open first end 62 of the calibration waveguide 60 to form a substantially leak-proof seal. As discussed above, the system 10 automatically compensates for well-defined air leaks, such as an open second end 64, but cannot compensate for unpredictable air leaks such as might occur along the side of the eartip 58.

In step 124, the system 10 generates the electrical stimulus signal $e_i$ (optionally determined in the stimulus generation phase of operation) and delivers it to the DAC 20. The system 10 measures the calibration pressure response $p^c$. In one embodiment, the length of the calibration waveguide 60 is sufficiently long and the duration of the electrical stimulus signal $e_i$ is sufficiently short so that the initial or incident pressure response $p_i$ is due only to the response of the driver 24 to the signal from the DAC 20, and does not include any sound reflections from the second end 64 or other discontinuity of the calibration waveguide 60. The duration of the electrical stimulus signal $e_i$ is also sufficiently short that the acoustical output of the driver 24 has died away before the first reflection from the second end 64 of the calibration waveguide 60 arrives at the probe assembly 50. This is the criterion of separability. However, as will be discussed in detail below, there are signal processing techniques that permit separability of the incident and first reflected signals even if there is some temporal overlap. Thus, the system 10 measures an incident response and a separate reflected response whether derived by temporal separation or signal processing. In step 126 the system 10 separates the pressure response into incident response and a first-reflected response. This first-reflected response is hereafter called the reflected response or reflected signal, when it is clear that higher-order reflected responses at larger delay times are not being discussed. It should be noted that, for convenience in performing the mathematical analysis, the system 10 uses the electrical stimulus signal $e_i$ derived in the stimulus generation phase as the stimulus signal in both the calibration phase and the evaluation phase. However, it is not necessary for the proper operation of the invention that the same signal be used in all three phases. It is important that the same signal be used in the calibration and evaluation phases, and the level of the electronic signal remain invariant so as to avoid nonlinear effects. These nonlinear effects are typically associated with source transducer nonlinearity and hydrodynamical nonlinearity in the acoustic flow emerging into the calibration waveguide, ear canal, or other waveguide to be tested. Any signal that is sufficiently short in duration relative to the round-trip acoustic travel time in the calibration waveguide 60 will be satisfactory.

The system 10 evaluates these two independent responses in step 128. It follows from the previous discussion of stimulus signal generation that $p_i^c=d$. There is no pressure response for times later than the incident response until the first reflected wave begins. After a time delay corresponding to the time for sound to propagate down the calibration waveguide 60 to the second end 64, be reflected, and propagate in the calibration waveguide back to the probe assembly 50, this reflected pressure signal $p_r^c$ is measured. The measured pressure signal also includes contributions from the re-reflection of the wave at the probe assembly 50. Thus, the total calibration waveguide pressure response $p_c$ is uniquely decomposed, for times sufficiently short that the second and higher-order reflected pulses have not yet arrived, by $$p^c(t) = p_i^c + p_r^c. \quad (5)$$

The reflected pressure wave is influenced by the viscous and thermal attenuation in the closed end 64 of the calibration waveguide 60. Previous systems that use calibration waveguides do not account for such effects and are thus incapable of accurate calibration and measurement. The system 10 employs an analytical representation of these viscothermal processes in terms of the reflection function $r^c$ of the closed tube. The model for this reflection function depends upon tube radius, the thermodynamic constants of air, and the tube length. A detailed analysis of the cylindrical tube model for the calibration waveguide 60 is provided below.

The only significant uncertainty in the measurement of the reflection function $r^c$ is in the tube length, which can vary depending on the insertion depth of the probe assembly 50. One can also regard fluctuations in the thermodynamic constants due to changes in ambient temperature as producing an equivalent change in the equivalent tube length, or else, the ambient temperature may be considered as an additional input to parameterize the temperature dependence of the thermodynamic constants in the model using well-known techniques. In step 132, the system 10 generates a model reflection function for the calibration waveguide 60 using an estimated value of the length L of the calibration waveguide. In step 134, the system 10 performs an analysis to calculate the tube length that gives the best fit between the measured reflection function and the model reflection function for the cylindrical tube. Detailed mathematical analysis of these steps are provided below. In step 136, the system 10 generates a new model reflection function for the calibration waveguide 60 based on an accurate determination of the length L of the calibration waveguide. In step 138, the system 10 uses the new model reflection function to accurately characterize the transfer characteristics of the measurement subsystem 57 (see FIG. 1). The system ends the calibration phase in step 140. In an alternative embodiment, the calibration waveguide 60 may be designed with a mechanical stop (not shown) so that the eartip 58 (see FIG. 2) is inserted at a fixed depth within the open first end 62. This eliminates the need for steps 134-138 that determine a refined tube length and new model function based on the refined tube length. In this alternative embodiment, the model function generated in step 132 is used by the system 10.

The frequency-domain representation of the Thevenin equivalent circuit is:

$$p^T(f) - p(f) = Z^T(f)u(f), \quad (6)$$

$$p(f) = Z(f)u(f),$$

where p is the total acoustic pressure at the tip of the probe assembly 50, u is the total volume flow through the probe tip, and Z is the acoustic impedance of the air column (or ear canal) into which the probe assembly is inserted. The Thevenin impedance $Z^T(f)$ can be written in terms of the Thevenin reflection coefficient $R^T$, implicitly defined by:

$$Z^T(f) = Z_c \frac{(1 + R^T)}{(1 - R^T)} \quad (7a)$$

where the characteristic impedance of the air column is $Z_c = \rho c/S$ such that the equilibrium air density is $\rho$, and the free-space phase velocity of sound is c, and the entryway area of the air column is S. The impedance $Z(f)$ of the unknown load can also be written in terms of the reflection coefficient $R(f)$ of the unknown load, which in the case of an ear-canal measurement is the input impedance at the probe tip in the ear canal. This is illustrated by the following equation:

$$Z(f) = Z_c \frac{(1 + R)}{(1 - R)} \quad (7b)$$

which is similar in form to equation (7a).

Because the acoustic signal applied to calibration waveguide 60 (or the ear canal) is a band-limited impulse it is convenient to work directly in the time domain, however, the principles of the present invention are equally applicable to calculations in the frequency domain. If one assumes that the probe assembly 50 is inserted into a cylindrical calibration waveguide 60 of sufficiently long length L that the source signal from the driver 24 ends before the first reflection arrives, then the initial signal detected by the microphone 30 will only be from the driver and not from reflected energy and the signal detected by the microphone after the first reflection will only be from reflections and not from the driver. The subscript 1 denotes a first time interval in which variables are non-zero only for times such that $0 \leq t < 2L/c$, and the subscript 2 denotes a second time interval in which variables are non-zero only for times $2L/c \leq t < 4L/c$. Then the Thevenin circuit equations can be transformed into the time domain with the result, $$2p_i^c{}_1(t) = 2p_1^c(t) - p^T * \{\delta - r^T\}, \quad (8)$$

$$p_r^c{}_2(t) = r^c * p_i^c{}_1 \quad (9)$$

where $\delta$ is the continuous-time delta-function, $r^T$ is the Thevenin reflection function, defined as the inverse Fourier transform of the Thevenin reflection coefficient $R^T$, and the reflection function $r^c$ of the cylindrical tube model is given below. Before the first reflection from the closed end 64 of the calibration waveguide 60 arrives, the pressure signal contains only an outgoing wave so that $p_1^c = p_i^c{}_1$. Equation (8) shows that the Thevenin source waveform $p^T$ is entirely contained in the first time interval, although the incident pressure wave depends also on the Thevenin reflection function $r^T$. The first reflected signal from the closed end 64 of the calibration waveguide 60 is $p_r^c{}_2$ whose subsequent reflection from the probe assembly 50 gives rise to another outgoing wave $p_i^c{}_2$. The Thevenin circuit relation is $$p_i^c{}_2(t) = r^T * p_r^c{}_2 = r^T * r^c * p_i^c{}_1, \quad (10)$$

so that the total tube pressure $p_2^c$ at the beginning of the second time interval is given by adding equations (9) and (10) with the result $$p_2^c(t) = r^c * p_1^c * \{\delta + r^T\}. \quad (11)$$

This pressure $p_2^c(t)$ can be extracted from the measured pressure response $p^c(t)$ because of the separability of the incident and first-reflected waveforms. The direct approach to solving for the Thevenin parameters is to solve equation (11) using deconvolution for $r^T$, followed by solving equation (8) using deconvolution for $p^T$. A more accurate approach is proposed below to utilize these two equations. This concludes the calibration phase of the system 10 in Reflectance Technique I.

The probe assembly 50 is inserted into the ear canal and the pressure response p is measured. Because of the short length of the ear-canal and the finite sample rate of the DAC 20 and ADC 40, the incident pressure wave from the sound source and the reflected pressure wave from the eardrum are superposed in time. Prior art systems cannot readily evaluate such signals because their overlap in time precludes separability. One prior art system attempts to separate the incident signal and reflected signal by placing a long tube in the patient's ear with the sound source at the end of the long tube. However, this approach is impractical in a clinical setting and is virtually impossible to use in small children. In contrast, the system 10 has determined the characteristics of the measurement subsystem 57 (see FIG. 1) in the calibration phase. This permits the system 10 to accurately analyze the overlapping incident and reflected waveforms without the use of cumbersome tubes protruding from the patient's ear.

In the frequency domain, suppose that the Thevenin parameters have been measured and the pressure response p is measured at the input to an unknown impedance Z. This impedance is calculated using the well-known "voltage divider" equation:

$$\frac{p(f)}{p^T(f)} = \frac{Z(f)}{Z(f) + Z^T(f)} \quad (12)$$

This is transformed by changing all impedances into reflection coefficients, rearranging terms to eliminate all terms in the denominator, and inverse Fourier transforming the equation into the time domain. The resulting equation in the time domain is $$2p*\{\delta - r^* r^T\} = p^T * \{\delta - r^T\} * \{\delta + r\}, \quad (13)$$

where r(t) is the reflection function of the unknown air column (e.g., the ear), defined as the inverse Fourier transform of the pressure reflection coefficient R(f) of the unknown load in equation (7b). Using the direct approach, one can substitute the functions $p^T$ and $r^T$ calculated by deconvolution and solve equation (13) for the single unknown r using deconvolution. However, the direct approach has relatively large error, because any error in the initial pair of deconvolutions contributes much larger error in the subsequent deconvolution.

A better approach, used by the system 10, is to transform equation (13) using equation (8) so that:

$$p*\{\delta - r^* r^T\} = p_1^c * \{\delta + r\}, \quad (14)$$

thereby eliminating $p^T$. Equation (14) is rearranged to provide the following:

$$p(t) - p_1^c(t) = r * \{-p + p_1^c + p*[\delta + r^T]\}. \quad (15)$$

The object is to eliminate $r^T$ from this equation (15) using equation (11). This is achieved by convolving the above equation with $r^c * p_1^c$ with the result $$s(t) = r*q, \quad (16)$$

where the function s is defined by $$s(t) = r^c * p_1^c * \{p - p_1^c\}, \quad (17)$$

and where the function q is defined by $$q(t) = -s + p*p_2^c. \quad (18)$$

Equation (16) is solved for the unknown reflection function r by a single deconvolution:

$$r(t) = \text{DECONV}(q, s). \quad (19)$$

While the analysis described above is derived based upon the use of a Thevenin equivalent circuit, it does not depend on the explicit evaluation of these Thevenin parameters. This solution for r(t) is valid for times $0 \leq t < 2L/c$ for calibration waveguide length L, because the derivation is based upon the incident and first reflection in the calibration waveguide, via equation (11). The use of a single deconvolution is much more accurate in practical applications than using two deconvolutions of equations (8) and (11), when calculations are performed in the time domain. The corresponding frequency-domain versions of equations (16)–(18) in terms of Fourier transforms are:

$$R(f) = s(f)/q(f), \quad (20)$$

$$s(f) = R^c(f) p_1^c(f) \{p(f) - p_1^c(f)\}, \quad (21)$$

$$q(f) = -s(f) + p(f) p_2^c(f). \quad (22)$$

Cylindrical Tube Model

The reflection function $r^c(t)$ introduced earlier for a cylindrical tube of length L and cross-sectional radius a describes the propagation delay ($\tau = 2L/c$) and viscothermal losses for a sound wave traveling down the tube, reflecting from its closed far end, and traveling back up the tube to the probe assembly. For $t \leq \tau, r^c = 0$. For $t > \tau$, $$r^c(t) = \frac{1}{\sqrt{\pi}} \frac{A}{(t-\tau)^{3/2}} e^{-A^2/(t-\tau)}, \quad (23)$$

where $$A = \alpha \frac{L}{c}, \quad (24)$$

$$\alpha = \sqrt{\frac{l_v}{c}} + (\gamma - 1)\sqrt{\frac{l_t}{c}}, \quad (25)$$

$$l_v = \frac{\eta}{\rho c}, \quad (26)$$

$$l_t = \frac{\kappa}{\rho c C_p}, \quad (27)$$

such that $\eta$ is the shear viscosity of air, $\kappa$ is the thermal conductivity of air, $C_p$ is the specific heat of air at constant pressure, and $\gamma$ is the ratio of specific heats. The implementation uses discrete-time signal processing, so the continuous-time reflection functions must be converted to their discrete-time counterparts, by multiplication of the continuous-time function by the sample period using conventional signal processing techniques. The sample rate of the DAC 20 and the ADC 40 should be at full audio bandwidth, corresponding to sample rates in the range of 40–50 kHz. The cylindrical tube may have its far end open, or terminated by an arbitrary linear response function, and the changes to the reflection function are well known to those skilled in the art. The frequencydomain expression for the reflection coefficient $R^c(f)$ is discussed below.

In practical applications, these thermodynamic constants are known and the radius of the calibration waveguide 60 is easily measured. The tube length L is known approximately, but any insertion distance of the probe assembly 50 into the calibration waveguide 60 effectively reduces the acoustic length of the tube. Variations in the acoustic length of the calibration waveguide 60 affect the value of the propagation delay τ and the value of A thus affecting the model reflection function of equation (23). A procedure is used by the system 10 to optimally estimate the length based upon an approximate starting point. The tube model $r^c$ is calculated using equation (23) and the calibration measurements are carried out. The evaluation phase described above can be applied to the calibration waveguide 60 itself to estimate its reflection function. The functions s and q are calculated using the calibration waveguide data and equations (17)–(18). When the model length is correct, the signal q has a single peak. When the model length is slightly incorrect, the signal q has an additional peak at a time delay of 2L/c. Using conventional one-dimensional minimization techniques, the energy in the signal q is minimized by varying the model length L as follows:

1. Approximate the tube length L and calculate the propagation delay r to the nearest sample D. This delay is the initial value of s[D].
2. Calculate s and q. The corresponding window of the first reflection begins at s[n+D] and extends to s[n+2D–1] where s[n] denotes the value of s at the nth sample. This window brackets the second peak of q.
3. Vary the model tube length L to minimize the energy of s in the first reflection window over a range of times in such that n+D≤m≤n+2D–1. This change in L means calculating a new model reflection $r_c$ followed by recalculating s and q. Iterate until the optimum length L is calculated.

In this manner, the system 10 can adjust the value of the length L of the calibration waveguide 60 to compensate for variations in the position of the probe assembly 50 within the calibration waveguide. With an accurate estimate of the length L, the transfer characteristics of the measurement subsystem 57 can be accurately determined in step 138 of FIG. 5.

Figure 6:
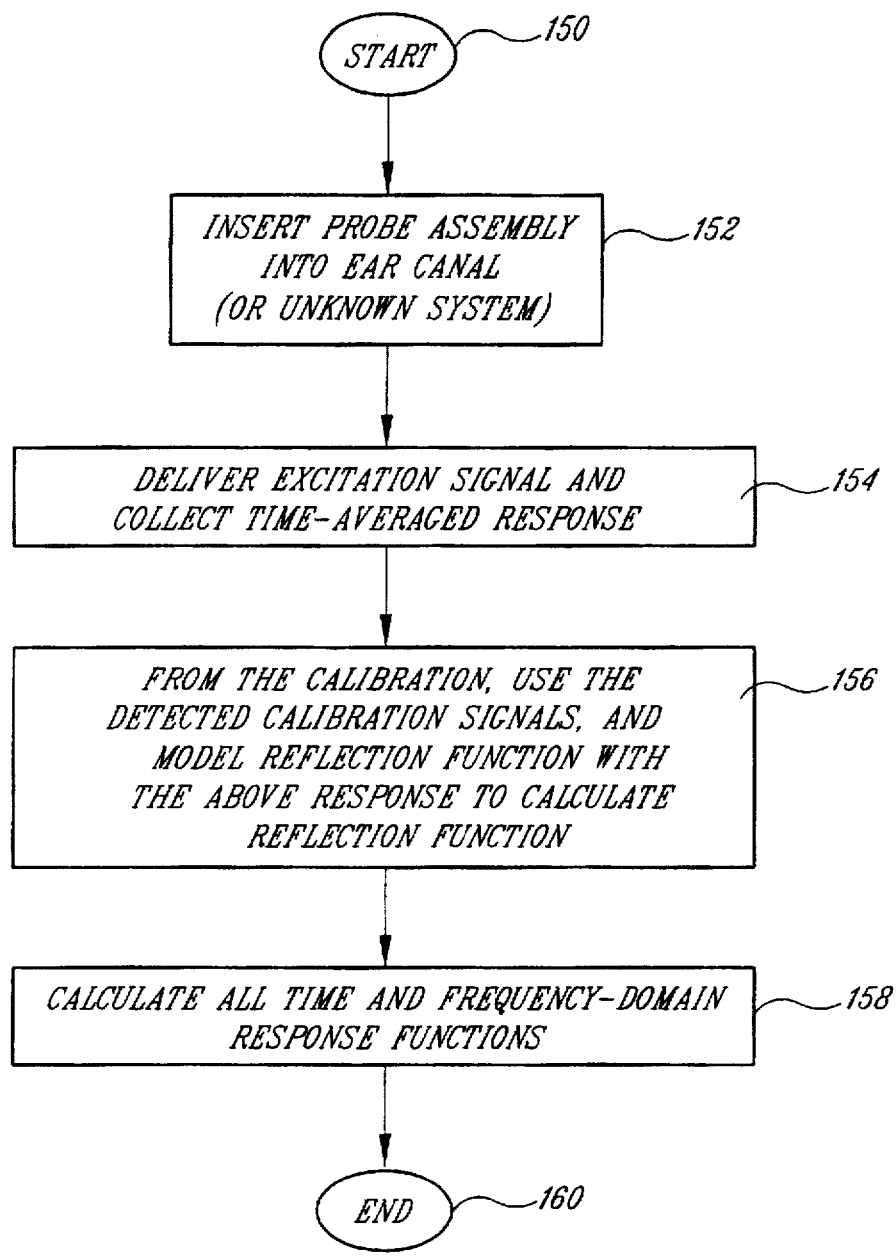
FIG. 6 is a flowchart of the linear response measurement procedure used by the system of FIG. 1.

The system 10 is capable of measuring the pressure response of the ear canal or other acoustic waveguide and determining the impulse response, and other acoustic properties of the acoustic waveguide in terms of the reflection coefficient using well-known transformations. The measurement of the unknown acoustic waveguide is described below in conjunction with the flowchart of FIG. 6. At the start 150, the stimulus signal has been determined in the manner discussed above, and the system 10 has been calibrated. In step 152 the user places the probe assembly 50 (see FIG. 2) into the ear canal (or other unknown system). In step 154, the driver 24 delivers the stimulus signal, and the microphone 30 detects both the stimulus signal and reflected energy, as discussed above.

In step 156 the system 10 uses the detected calibration signals as well as the reflection function data from the calibration waveguide 60 to calculate the reflection function of the unknown acoustic waveguide (e.g., the ear or other system). In step 158, the system calculates the time-domain and frequency-domain response functions for the unknown system in the manner previously described. The system ends the measurement phase in step 160.

It is often convenient to calibrate in the frequency domain, and the frequency-domain version of the cylindrical calibration waveguide model is most appropriate. The reflection coefficient $R^c(f)$ in a closed cylindrical tube of length L is $$R^c(f)=e^{-2\Gamma L}, \quad (28)$$

where the complex propagation wavenumber Γ varies with the radius of the calibration waveguide, frequency, and the viscothermal constants of air that appear in equations (25)–(27). Explicit expressions for Γ are well known, for example, in Keefe ("Acoustical wave propagation in cylindrical ducts: Transmission line parameter approximations for isothermal and non-isothermal boundary conditions," *J. Acoust. Soc. Am.* 75:58–62, 1984).

Time-Stretched Stimuli and Time-Compressed Responses

The above description illustrates a technique for the characterization of the acoustic transfer characteristic of the measurement subsystem 57 (see FIG. 1) by using a stimulus signal that is short in duration so that the signal from the driver 24 has died away before the first reflected signal from the closed end of the calibration waveguide 60 arrives at the microphone 30. However, signal processing techniques are known in the art that permit the separation of the incident and reflected signals even though there may be some temporal overlap. A technique described in Aoshima, Nobuharu, "Computer-Generated Pulse Signal Applied for Sound Measurements," *Journal of the Acoustical Society of America* 69:1484–88, 1981, uses a chirp as a test signal where the chirp is a time-stretched, band-limited impulse. This time-stretching factor must be explicitly known.

The presently preferred embodiment of the system uses a pulse signal so that the incident signal and the reflected signal are temporally separated. This simplifies the signal processing required by the system 10. The disadvantage of the narrow pulse signal is that, for a given signal-to-noise ratio, the pulse system requires a much higher peak amplitude than the chirp signal. This may potentially cause an overload of the driver 24. The chirp signal distributes the spectral energy over a longer time duration when compared to the band-limited impulse (i.e., pulse signals). Because the time-stretched signal has the same spectral power as the original pulse, the peak levels of the time-stretched signal are much lower than the peak levels of the corresponding short duration pulse. It is well known that peak amplitudes in the driver 24 are the primary cause of nonlinearities; the use of the time-stretched signal reduces the possibility of nonlinearities in the driver or other system components. For a given peak threshold, more power can be delivered by the driver 24 using the chirp signal than using the short duration pulse. Thus, the use of a chirp signal gives better signal-to-noise levels than the pulse-based systems. The disadvantage of the chirp signal approach is that more complex signal processing is required. However, this signal processing is well-known in the art, and need not be described in detail herein.

The chirp processing is based on the property that a chirp is simply a time-stretched pulse. Thus, one can begin by designing an arbitrary short duration pulse, by FIR, IIR, or other design methods, as discussed above. The chirp signal is designed by applying a conventional allpass filter to the short duration pulse. The output in the time domain has the same spectral power as the original pulse, but the time-domain waveform is stretched by the allpass filter response. Since the "pulse" is a band-limited signal, then one can use a slightly more general formulation in which one can essentially use a bandpass filter instead of an allpass. But care must be taken in applying the inverse filter, since the inverse bandpass filter does not exist, unless the pass band of the inverse filter is restricted to avoid singularities. The constraints are that the output of the allpass or specialized bandpass filter increase the effective duration of the output signal over the input signal, and that the corresponding quasi-inverse filter, if not a true inverse in the case of a specialized bandpass filter, be sufficiently close that the convolution of the filter with its quasi-inverse have an impulse response whose duration is very short compared to the round-trip delay time in the calibration waveguide.

Because such a filter behaves similarly to an allpass filter, it is denoted as an allpass filter and its quasi-inverse is denoted as an inverse allpass filter in subsequent discussion. Useful allpass filters, for a pulse-like input signal, include those that generate a chirp signal whose group delay varies linearly with frequency, as in Aoshima, *Journal of the Acoustical Society of America* 69:1484–88, 1981, and one whose group delay varies logarithmically with frequency. Design techniques for the allpass filter are well known, and will not be discussed herein.

The microphone 30 measures a response that has a similar allpass characteristic as the chirp stimulus, but modified by the acoustic transfer characteristics of the measurement subsystem 57 and the acoustic transfer characteristics of the calibration waveguide 60 or other waveguide. A filter that is an inverse to the original allpass filter is applied to the detected electrical signal 34. This inverse filter is also an allpass filter, and its design is well-known in the art. The output from the inverse filter is a time-compressed pressure response. The spectral level response is not modified, and the result is a short duration pressure response. So long as the impulse response of the driver 24 is much less than the time delay between the incident signal and the reflected signal in the calibration waveguide, then the incident and reflected, time-compressed, pressure responses are easily separated. These time-compressed incident and first reflected signals are processed in the same manner as the pulse signal.

The time-stretching and compression technique discussed above is described in the flow chart of FIG. 7. At the start 200, the system 10 has no time-stretched signal. In step 202, the system 10 generates an initial electrical signal input corresponding to a short duration acoustic stimulus. In step 204, the system uses an allpass filter on the electrical input signal to generate a time-stretched electrical input signal. In step 206, the system 10 delivers the time-stretched electrical input signal to the driver 24 (see FIG. 1). In step 208, the system collects a time-averaged response signal as in the manner described above. In step 210, the system filters the response signal using an inverse allpass filter to generate a time-compressed response signal. In step 212, the system separates the time-compressed response signal into an incident signal and a first reflected signal. In step 214, the system 10 processes the separated signals in the manner previously described. The system ends the time-stretching and compression process in step 216.

The time-stretching and compression techniques discussed above may also be applied to the stimulus design phase of operation to design an electrical input signal having improved signal to noise ratio when compared to pulse techniques. The system 10 time-stretches the initial electrical signal $e_s$ using the first allpass filter and delivers the time-stretched initial electrical signal to the driver 24. The detected electrical signal 34 is time-compressed by the inverse allpass filter to permit the separation of the incident and first reflected signals. The separated signals are processed in the manner previously described to design the electrical stimulus signal $e_i$ that will cause the driver 24 to generate the desired incident pressure signal $p_i$. The electrical stimulus signal $e_i$ may also be time-stretched and compressed as discussed above. The combined techniques of time-stretching of the stimuli and time-compression of the pressure responses may also be applied to all the other reflectance, impedance and admittance measurement techniques described below.

Reflectance Technique II

In the previous discussion, the reflectance model utilized only the incident response and the first reflected response. It is possible to use an alternative reflectance in the system 10 which includes all the reflected signals in data acquired in the calibration waveguide 60. Time-domain deconvolution is most efficient when the responses are of brief duration, yet this brief duration sets an upper limit to the duration of the reflection function that can be measured. An alternative measurement method is constructed that enables measurements of longer reflection functions at the cost of increased computation. It is also well-suited for frequency-domain measurements of the reflection coefficient.

Equation (14) is written for a calibration waveguide 60 (see FIG. 2) for which $p(t)=p^c(t)$ and $r(t)=r^c(t)$, with the result that $$p^c * \{\delta - r^c * r^T\} = p_i^c * \{\delta + r^c\}, \tag{29}$$

The object is to eliminate $r^T$ from these equations. This is achieved by convolving equation (14) with $r^c *p^c$ and convolving equation (29) with $r*p$ and subtracting. The resulting equation for the reflection function $r(t)$ is $$\hat{s} = r * \hat{q}, \tag{30}$$

where the function $\hat{s}$ and $\hat{q}$ are defined by $$\hat{s}(t) = r^c * p^c * \{p - p^0\}, \; \hat{q}(t) = p * (p^c - p^0 - r^c * p^0) + r^c * p^0 * p^c, \tag{31}$$

and where, for simplicity, the incident pressure field $p_i^c$ is denoted by $p^0$. The solution for $r$ is obtained by deconvolution of equation (30). The durations of $\hat{s}(t)$ and $\hat{q}(t)$ are much longer than those of $s(t)$ and $q(t)$ in equations (17) and (18), so that the deconvolution of equation (30) involves significantly more computation. The benefit is that the reflection function can be calculated over longer time durations, on the order of the overall duration of data collection.

In a frequency-domain experiment, the Fourier transforms of equations (14) and (29) are solved for the unknown reflection coefficient with the result $$R(f) = \frac{p - p^0}{R^T p + p^0}, \tag{32}$$

here the reflectance of the probe assembly 50 is $$R^T(f) = \frac{p^c - p^0(1 + R^c)}{R^c p^c}, \tag{33}$$

There is no possibility of adjusting the length in this formulation (or in the corresponding time-domain formulation). When equation (32) is evaluated for the calibration waveguide 60 with $p(f)=p^c(f)$, the result is that $R(f)=R^c(f)$ is identically satisfied. In the frequency domain, there is no significant penalty to utilizing the full calibration-tube response, and this should lead to improved estimates of the reflection coefficient $R(f)$.

The probe assembly 50 is affixed to the calibration waveguide 60 in such a way that the length L is accurately determined such as by a mechanical stop (not shown), as previously discussed. The calibration in these single-tube techniques (Reflectance Techniques I and II) can be checked by comparing the response $p^c$ measured by the operator of the instrument with a response stored in the system. This enables the system to measure any change in the incident signal, which test the ability of the probe to generate an acoustic signal according to system specifications. It also enables the system to measure any change in the first-reflected signal to validate that the source reflectance of the probe has not changed due to the presence of a leak or other mechanical problem. Lastly, the overall noise level of the probe can be checked by the system.

Reflectance Technique III (Multi-Tube Technique)

The system 10 has been previously described for use with the single calibration waveguide 60. However, it is possible to include length optimization when a second calibration waveguide 60 of a different length is used. This allows averaging of two independent calculations of energy or pressure reflected from the probe, which is not possible in the prior art. Furthermore, this technique is easily generalized to utilize responses measured in a plurality of calibration waveguides.

The single-tube Reflectance Techniques I and II estimate two independent parameters using the single calibration waveguide 60, whereas prior art systems have needed two or more calibration waveguides, or more generally, two or more calibration loads, to estimate two parameters. For example, U.S. Pat. No. 4,289,143, issued on Sep. 15, 1981 to Canavesio et al., uses two cavities that are assumed to have no acoustic losses due to viscothermal processes. His method of measuring impedance does not use separability, and he does not specify how to measure reflectance. Reflectance Technique III used by the system 10 obtains three estimates of two parameters using two calibration loads, or, more generally, (M+1) estimates of two parameters using M calibration loads for M>2. This allows averaging of responses to improve the estimate of acoustic energy reflected from the probe assembly 50, and it allows optimization of the length of each calibration waveguide 60 to further increase the accuracy.

The preferred embodiment of this method is in the frequency domain, although it is straightforward to construct a time-domain version. It is also possible to make some calculations in the frequency domain and others in the time domain. Begin in the frequency domain for M calibration waveguides with pressure responses $p^i$ and model reflection functions $R^i$, where i varies from 1 to M. It should be noted that, for the sake of clarity, the simplification of notation wherein the model reflection function of the i-th tube is $R^i$ rather than $R^{ci}$, and the calibration waveguide response is $p^i$ rather than $p^{ci}$. The source reflectance $R^{Ti}$ estimated for the i-th tube is given using equation (33) as $$R^{Ti} = \frac{p^i - p^0(1 + R^i)}{R^i p^i} \quad (34)$$

The M values of $R^{Ti}$ are used to estimate the single source reflectance $R^T$. The system 10 averages the values with suitably chosen weighting factors $w_i$ so that $$R^T = \sum_{i=1}^{M} w_i R^{Ti} \quad (35)$$

with the normalization that $$1 = \sum_{i=1}^{M} w_i \quad (36)$$

One embodiment is to choose the weighting factor equal ($w_i=1/M$) so that the sum is a simple average.

The preferred embodiment takes account of the fact that the source reflectance enters due to the round-trip reflection of energy from the opposite end of the calibration waveguide 60. For example, suppose there are only two calibration waveguides 60. The first calibration waveguide 60 must be sufficiently long that the incident and reflected pressure signals can be decomposed, so that the incident field $p_1^c = p^0$ is known. The problem is that the reflected pressure amplitude is diminished from this incident pressure amplitude at high frequencies. It follows that the estimate of the source reflectance, denoted $R^{T1}$ in tube 1, becomes inaccurate at high frequencies.

However, the second calibration waveguide 60 may be chosen to be much shorter in length, without regard for the overlap of incident and first-reflected pressure signals in time. In the frequency domain, this substantially increases the amplitude of the reflected pressure, and thus leads to a more accurate estimate of the source reflectance, denoted $R^{T2}$ in tube 2. This is built into the weighting factor by choosing it such that $w_i$ increases with increasing $|R^i|$. A class of embodiments is to choose the i-th weight proportional to some power of $|R^i|$, as follows:

$$w_i = \frac{|R^i|^v}{\sum_i |R^i|^v}, \quad (37)$$

where v>0. The preferred embodiment is the choice v=1. Alternatively, the weighting factors can be chosen proportional to pressure magnitude or sound pressure level, so that the weighting is small at frequencies for which the signal to noise ratio is low, or some combination of these variables with a function of the model reflectance.

Given the estimate of source reflectance $R^T$, the estimate $R_e^i$ of the i-th tube reflectance is calculated via equation (32) as $$R_e^i(f) = \frac{p^i - p^0}{R^T p^i + p^0} \quad (38)$$

In contrast to Reflectance Technique II, this estimate of source reflectance for the i-th tube is not identically equal to the model reflectance $R^i$ for the i-th tube. The error $\epsilon^i[k]$ between the i-th estimate and model tube reflectance at the k-th frequency is defined as $$\epsilon^i[k] = R_e^i - R^i \quad (39)$$

The length $L^i$ of the i-th tube may not be precisely known, for example, due to uncertainties in the insertion depth of the probe assembly 50 within the calibration waveguide 60. Another source of error is the temperature dependence of the sound speed, which can result in a change in the effective, or functional, lengths of the calibration waveguides 60. The global error function E is defined by summing the magnitude squared of the error defined above over all calibration waveguide responses and over the frequency range of interest, bounded by the lower frequency index $k_l$ and upper index $k_u$, with the result $$E = \frac{1}{M(k_u - k_l + 1)} \sum_{i=1}^{M} \sum_{K=K_l}^{k_u} |\epsilon^i[k]|^2. \quad (40)$$

The error function varies with the choice of tube lengths, and is minimized by an optimal selection of tube lengths. A M-th order least-mean-squares optimization is used to choose the tube lengths $L^i$. The preferred embodiment is the M-th order minimization technique known in the art, and described in Keefe et al., *J Acoust. Soc. Am.* 91:470–485, 1992.

The iterative technique is as follows:

1. The pressure responses $p^i$ are measured in the set of calibration waveguides.
2. The first tube, taken to be the longest tube in the set, is chosen to be sufficiently long that the incident and reflected waveforms can be decomposed. The incident waveform is chosen using the previously described property of separability.
3. Choose initial estimates of tube length $L^i$.
4. Calculate model reflectance $R^i$.
5. Calculate source reflectance $R^T$ from equation (35).
6. Calculate the global error function from equation (40).
7. Minimize the global error function by choosing new estimates of tube lengths $L^i$.

8. Iterate on steps 4–7 until the reduction in the global error function is sufficiently small.

It is anticipated that the choice of two calibration waveguides (M=2) is of particular interest due to its relative simplicity. The fewer the number of tubes, the faster is the calibration. Using two calibration waveguides 60 allows the selection of the first long tube to calculate $p^0$ and the second short tube to increase the accuracy of the calculation of $R^T$.

The final reflectance of the unknown system is calculated in the frequency domain using equation (32).

To calculate a time-domain reflectance, one approach is to solve for the frequency-domain reflectance using the above method, and then calculate the time-domain reflectance using the inverse discrete Fourier Transform (DFT). The preferred embodiment is to calculate the time-domain reflectance in the time domain.

Since there are M calibration waveguides, there are now M relations of the form of equations (30)–(31). The functions $s^i$ and $q^i$ (for the sake of simplicity, the superscript carets on the corresponding symbols introduced in equation (31) have been omitted) are defined based upon the i-th calibration waveguide model and pressure response in the time domain by:

$$s^i = r^{i*} p^{i*} \{p - p^0\}, \quad q^i = p*(p^i - p^0 - r^{i*} p^0) + r^{i*} p^{0*} p^i \tag{41}$$

so that M estimates of the unknown r are obtained by deconvolving $$s^i = r * q^i. \tag{42}$$

A weighted time-domain formulation is constructed by defining $s_w^i$ and $q_w^i$ by $$s_w^i = w * s^i, \quad q_w^i = w * q^i. \tag{43}$$

in terms of weighting time series $w$. The reflectance $r$ satisfies $s_w^i = r * q_w^i$ for each i. The weighted time-domain reflectance is calculated by deconvolving $$\sum_{i=1}^{M} s_w^i = r * \sum_{i=1}^{M} q_w^i \tag{44}$$

One embodiment is to choose equal weighting so that $w = (1/M)\epsilon$. The preferred embodiment, following the discussion in the frequency-domain solution, is to weight by the reflectance so that $$w^i = r^i \tag{45}$$

Alternative choices of weighting may be used based upon sound pressure, or combinations of reflectance and sound pressure, as described earlier.

The length optimization carried out in the time domain is analogous to that in the frequency domain, except that a significant number of extra deconvolutions need to be calculated. To specify that the source reflectance is independent of the Thevenin circuit representation, it is denoted in the time domain as $r^0(t)$ rather than $r^T(t)$, and in the frequency domain as $R^0(f)$ rather than $R^T(f)$. Therefore, the reflectance circuit parameters are $r^0$ and $p^0$. The source pressure $p^0$ is specified by the separability condition in the longest tube, whereas $r^0$ is calculated iteratively based upon the model reflectance $r^i$ calculated using the current estimate of the tube length and the set of responses measured in the calibration waveguides.

Equation (29) for the i-th calibration waveguide is $$p^{i*}\{\delta - r^{i*} r^0\} = p^{0*} \{\delta + r^i\} \tag{46}$$

The responses $p^i$ and $p^0$ are known and the model reflection function $r^i$ is calculated based upon the current length estimate, so that the only unknown is the source reflectance $r^0$. This source reflectance could be solved for each tube, and one would obtain different values due to the presence of noise and small errors in the model reflection function. Denote the i-th estimate of the source reflectance by $r^{0i}$. It is evaluated from the above by deconvolving $$q^{0i*} r^{0i} = s^{0i}, \quad q^{0i} = r^{i*} p^i, \quad s^{0i} = p^i - r^{i*} p^0. \tag{47}$$

The average value of the source reflectance, denoted by $r^0$, is calculated from $$r^0 = (1/M) \sum_{i=1}^{M} r^{0i}, \tag{48}$$

or, if a weighted convolution sum is chosen, from $$r^0 = \sum_{i=1}^{M} w^{i*} r^{0i}. \tag{49}$$

This average value of source reflectance is substituted into equation (46), and the corresponding model reflectance is replaced by its estimated value $r_e^i$ as follows:

$$p^{i*}\{\delta - r_e^{i*} r^0\} = p^{0*} \{\delta + r_e^i\} \tag{50}$$

The solution $r_e^i$ in the i-th tube is found by deconvolving $$q_e^{i*} r_e^i = s_e^i \tag{51}$$

where $$q_e^i = r^{0*} p^i + p^0, \quad s_e^i = p^i - p^0. \tag{52}$$

The error $\epsilon^i[k]$ between the i-th tube estimate and model reflectance at the k-th discrete time step is defined as $$\epsilon^i[k] = r_e^i[k] - r^i[k]. \tag{53}$$

The next iterated set of tube length estimates are calculated by minimizing the square of this error across all tubes and all time steps. This is the time-domain analog to equation (40) in the frequency domain.

This length optimization technique requires (M+1) deconvolutions for each iteration on the set of lengths. This is computationally intensive, but the final calculation of the ear-canal reflectance is only dependent on a single deconvolution independent of the estimate of source reflectance $r^0$, i.e., equation (44).

An alternative technique for length optimization, which is the preferred embodiment, is to carry it out in the frequency domain as described above, even though the ear-canal reflectance is calculated in the time domain from equation (44). The length optimization is only used to calculate the best set of tube lengths, which are then input to the time-domain model to calculate the model reflectance using equation (23). Whether optimized in the time or frequency domain, this "best" set of lengths can be used for the time-domain model reflectance, and thus used to calculate the time-domain ear-canal reflectance.

Reflectance, Impedance, and Admittance Technique IV

In the Technique IV to measure a linear response, the system 10 combines the ideas of the techniques described above, a modification of techniques described in Allen, J. B., *Peripheral Auditory Mechanisms*, Allen, J. et al., eds., 1985, and Keefe et al., *J. Acoust. Soc. Am.* 91:470–485, 1992, and the matrix regularization technique in Agulló et al., *J. Acoust. Soc. Am.* 97:1950–1957, 1995. The preferred embodiment is in the frequency domain, although the theory may also be formulated in the time domain. It is also possible to make some calculations in the frequency domain and others in the time domain. The basic idea is to calculate the two complex source parameters $p^o(f)$ and $R^o(f)$ using a system of responses measured in a set of M calibration waveguides, with $M \geq 2$. Model reflection functions are calculated using a set of lengths whose values may be optimized using an iterative procedure. Whereas multi-tube Technique III uses one tube response for which to calculate $p^o(f)$ and one or more tube response to calculate $R^o(f)$, Technique IV uses all the tube responses to calculate both $p^o(f)$ and $R^o(f)$.

An alternative class of embodiments to those based upon separability utilize measurements in a plurality of calibration waveguides. This plurality of responses, along with a calibration waveguide model that predicts an acoustic transfer response for each calibration waveguide, form a matrix system that can be used to calibrate the measurement system in the absence of a separability condition. It is well known for the Thevenin and Norton circuits, and it is also true for the reflectance circuit, that two or more calibration waveguides with known iso-level responses may be used to calculate the two quantities associated with the stimulus and the probe assembly. Should three or more calibration waveguides be used, the resulting system equations to calculate the two unknown quantities form an overdetermined system. It is well known that overdetermined systems are useful for reducing the influence of noise on the accuracy of the calibration. Even with two calibration tubes, the use of matrix regularization, to be described, can stabilize the solution for the two unknown quantities in the presence of noise. Prior-art overdetermined systems have been used to calibrate the Thevenin parameters of a measurement system in the frequency domain (Allen, J. B., "Measurement of Eardrum Acoustic Impedance," *Peripheral Auditory Mechanisms*, Allen, J. et al., eds., Springer-Verlag, New York, 1985; Keefe et al., *J. Acoust. Soc. Am.* 91:470–485, 1992).

These prior art systems are extended in the present invention to cover Thevenin, Norton and reflectance circuit representations in both frequency and time domains. The time-domain implementation replaces matrix multiplication by matrix convolution. The stage of matrix inversion in the frequency-domain representation is replaced by matrix deconvolution in the time domain. Prior-art systems give inaccurate calibrations when the pressure at the probe assembly is small in several of the tubes at a given frequency, leading to a small signal-to-noise ratio. The invention describes two novel solutions to this problem of noise contamination. The first is that the overdetermined system of equations include a plurality of weighting functions. These weighting functions attenuate the responses of particular calibration-waveguide measurements at frequencies where the pressure at the probe-assembly microphone is small or where the calibration waveguide reflects only small amounts of acoustic energy, and enhances the responses of other measurements where the signal to noise is robust. The second solution is based upon the recognition that the primary effect of noise is to de-stabilize the matrix inversion used in the frequency-domain method of solution. The matrix can be regularized, for example, by taking a linear combination of the matrix with a small-amplitude matrix that is invertible. This stabilizes, or is said to regularize, the matrix inversion and reduces inaccuracies in the calibration. Since the addition of the small-amplitude invertible matrix itself contributes small measurement inaccuracies, the amplitude of the invertible matrix can be iteratively adjusted in magnitude to trade-off good regularization properties with overall accuracy. Both solutions can also be applied to time-domain calibration representations. The weighting function becomes a function of time and the regularization is straightforward. Regularization in the time domain has been utilized in acoustic deconvolution procedures outside the scope of the present invention (Agulló, Cardona and Keefe, "Time-Domain Measurements of Reflection Functions for Discontinuities in Cylindro-Conical Waveguides," *J. Acoust. Soc. Am.* 97:1950–1957, 1995).

The starting relation is the reflectance circuit, using equation (32), for the i-th tube, which can be expressed in the form:

$$(1+R^i)p^o + R^i p^i R^o = p^i, i=1 \text{ to M}. \tag{54}$$

This system of equations can be written using an M×2 matrix A defined by $$A\vec{x} = \vec{y}, \tag{55}$$

where the matrix and 2×1 complex vector $\vec{x}$ and the M×1 complex vector $\vec{y}$ are defined by $$A(f) = \begin{pmatrix} w_1(1+R^1) & w_1 R^1 p^1 \\ w_2(1+R^2) & w_2 R^2 p^2 \\ \cdot & \cdot \\ \cdot & \cdot \\ w_M(1+R^M) & w_M R^M p^M \end{pmatrix}, \tag{56}$$

$$\vec{x}(f) = \begin{pmatrix} p^o(f) \\ R^o(f) \end{pmatrix},$$

$$\vec{y}(f) = \begin{pmatrix} w_1 p^1 \\ w_2 p^2 \\ \cdot \\ \cdot \\ w_M p^M \end{pmatrix},$$

and where weighting factors $w_i$ have been applied to the i-th row of the matrix A and vector $\vec{y}$. Each weighting factor is chosen to be positive, and the sum of the weighting factors over all tubes can be normalized to unity, without loss of generality. The unknown in the above is the two-component vector $\vec{x}(f)$ that quantifies the source/microphone circuit parameters, in this case, the incident pressure $p^o$ and source reflectance $R^o$.

In Allen, J. B., *Peripheral Auditory Mechanisms*, Allen, J. et al., eds., 1985 and Keefe et al., *J. Acoust. Soc. Am.* 91:470–485, 1992, a similar matrix equation, except for the inclusion of the arbitrary weighting factors wi, has been written in which the unknown two-component vector $\vec{x}(f)$ includes the Thevenin pressure $p^T$ and Thevenin impedance $Z^T$. It is well known to those skilled in the art that a corresponding matrix equation may be written in terms of a two-component vector composed of the Norton volume velocity and Norton admittance, because the Norton parameters can be expressed in terms of the Thevenin parameters.

With each change in $\vec{x}(f)$ comes straightforward changes in the matrix $A(f)$ and vector $\vec{y}(f)$.

Equations (55)–(56) form an overdetermined matrix system of equations when the number of rows (M) exceeds the number of columns (2), and there exists no unique solution for the unknown vector $\vec{x}$. The approximate least-squares solution is to calculate the vector $\vec{x}$ that minimizes the following norm:

$$\|A\vec{x} - \vec{y}\|. \tag{57}$$

The solution $\vec{x}$ is called the minimum norm solution, and $\vec{x}$ contains the measurement system parameters. The matrix equation is unstable if the singular values of the matrix A decay gradually to zero or if the ratio between the largest and smallest non-zero singular values becomes too large, as explained in "Matrix Computations," 2nd edition, Gene H. Golub and Charles F. Van Loan (John Hopkins University Press, 1989). If the matrix equation is not unstable, then it is stable, and the corresponding method of solution is well known.

The associate set of regularization methods is to calculate the vector $\vec{x}$ that minimizes the above norm subject to the side constraint the minimizes the norm $$\|L(\vec{x} - \vec{x}^\dagger)\| \tag{58}$$

based upon an initial estimate $\vec{x}^\dagger$. The solution $\vec{x}$ vector is called the minimum norm solution with regularization. The matrix L is selected, with typical selections being the identity matrix, and finite-difference approximations to the first or second derivative operator. Taking the identity matrix as an example, the side constraint requires that the trial solution $\vec{x}$ remain in the neighborhood of the initial estimate $\vec{x}^\dagger$ Any tendency towards instability in the solution vector is thereby controlled.

There exists a wide variety of both direct and indirect regularization methods equally applicable to an unstable system, or a matrix equation whose stability is unknown. Each of these regularization methods computes a stabilized solution to the system of equations. Direct regularization methods include Tikhonov regularization, least squares with a quadratic constraint, singular value decomposition (SVD), truncated SVD, modified truncated (SVD), and truncated generalized SVD, damped SVD, damped generalized SVD, maximum entropy regularization, and truncated total least squares. Indirect regularization methods are iterative in nature, and include conjugate gradient, LSQR, bidiagonalization with regularization, the v-method, and extension to general-form methods based upon applying preconditioning to any of the above iterative methods. These methods are described in "Regularization Tools: A Matlab Package for Analysis and Solution of Discrete Ill-Posed Problems," Version 2.0, Per Christian Hansen (Danish Computing Center for Research and Education, 1993). The preferred embodiment is the following indirect regularization method: preconditioned conjugate gradient using a matrix L that implements a finite-difference approximation to the second derivative.

An alternative method of regularization is to solve equation (55) using the SVD or the conjugate gradient method, combined with Tikhonov's procedure, as discussed by Agulló et al., *J. Acoust. Soc. Am.* 97:1950–1957, 1995. The time-domain analogs to these techniques are discussed later.

A significant difference between Technique IV in the system 10 and techniques discussed in Allen, J. B., *Periph-eral Auditory Mechanisms*, Allen, J. et al., eds., 1985 and Keefe et al., *J. Acoust. Soc. Am.* 91:470–485, 1992 is that the cited techniques are particularized to the impedance representation of the circuit parameters whereas Technique IV is generally applicable to impedance, admittance or reflectance circuit representations. The reflectance circuit representation may be advantageous.

Another significant difference between Technique IV and these cited techniques is that they do not use regularization to stabilize the pseudoinverse solution for the circuit parameters, and this increases error in the circuit parameters (in this case, Thevenin parameters) at certain frequencies because the impedance has poles and zeros that can lessen the numerical stability of the matrix inverse compared to that in the reflectance domain. In contrast to the impedance or admittance (e.g., the Norton circuit), the reflectance has no poles or zeros: it is a complex number whose magnitude at each frequency lies between 0–1, so that the need for regularization may be reduced.

A third significant difference between Technique IV and these cited techniques is that they do not have separate weighting factors for each calibration waveguide response, as does Technique IV. It is entirely possible to choose one set of weighting factors for use in calculating $p^0$ (row 1 of $\vec{x}$) and another in calculating $R^0$ (row 2 of $\vec{x}$). The matrix calculations then need to be repeated, since a change in the weighting factors changes the matrix A. The estimate of $R^0$ is anticipated to be better for the shorter tubes, for which the reflected energy is greater, particularly for higher frequencies. Thus, the weighting factor for the $R^0$ solution should be larger for calibration waveguides whose reflected energy is greater. A general class of embodiments for the $R^0$ solution, based upon a positive exponent v, is $$w_i^r = \frac{|R^i|^v}{\sum_i |R^i|^v}. \tag{59}$$

The estimate of the incident-wave pressure $p^0$ is anticipated to be better for the longer tubes, for which the reflected energy is less, particularly for higher frequencies. Thus, the weighting factor for the $p^0$ solution should be larger for calibration waveguides whose reflected energy is less. Using a positive exponent v, a general class of embodiments for the $p^0$ solution is $$w_i^p = \frac{1 - |R^i|^v}{\sum_i (1 - |R^i|^v)}. \tag{60}$$

The preferred embodiment in this case is the particular choice of weightings for v=1. Another class of weightings for the $p^0$ solution uses the weightings for the $R^0$ solution in equation (59) as follows:

$$w_i^p = \frac{1 - w_i^r}{M - 1} \tag{61}$$

This choice of weighting, which is also properly normalized, is the overall preferred embodiment because the calculations are somewhat reduced in complexity.

It is also possible to use an alternative set of weighting factors, proportional to some increasing function of spectral tube pressure. That is, the larger the pressure magnitude at a given frequency in a given calibration waveguide, the higher the weighting of that tube response at that particular frequency. Possible weightings are proportional to the pressure magnitude $|p^i|^\mu$ to some positive exponent $\mu$, or proportional to the logarithm of the pressure magnitude $\log |p^i|$, as in the decibel scale, or other function thereof relative to a minimum threshold. Weightings in the time domain, which enter the model as convolutions with a weighting waveform, are chosen by setting the weighting waveform of the i-th tube $w^i(t)$ proportional to $|p^i(t)|$, some increasing function of $|p^i(t)|$, or its short-time amplitude envelope. Such pressure weightings may also be applied in Technique III.

The set of lengths may be optimized using the identical iterative technique described in Technique III, based upon the use of equation (40). The reflectance of the unknown system is calculated in the frequency-domain using equation (32) with $p^o$ and $R^o$ calculated from the solution vector $\vec{x}$ in equation (56).

The discussion above centered around a frequency domain analysis for Technique IV. However, as discussed below, Technique IV is also applicable to time domain analysis. The starting relation is the time-domain reflectance circuit equation, analogous to equation (54) in the frequency domain.

$$(\delta + r^i) * p^0 + (r^i * p^i) * r^0 = p^i, \quad i=1 \text{ to } M. \tag{62}$$

This system of convolution equations can be written using a M×2 matrix A as $$A * \vec{x} = \vec{y}, \tag{63}$$

where the matrix, the 2×1 vector $\vec{x}$ and the M×1 vector $\vec{y}$ are defined by $$A(t) = \begin{pmatrix} w_1*(\delta + r^1) & w_1*r^1*p^1 \\ w_2*(\delta + r^2) & w_2*r^2*p^2 \\ \cdot & \cdot \\ \cdot & \cdot \\ \cdot & \cdot \\ w_M*(\delta + r^M) & w_M*r^M*p^M \end{pmatrix}, \tag{64}$$

$$\vec{x}(t) = \begin{pmatrix} p^0(t) \\ r^0(t) \end{pmatrix},$$

$$\vec{y}(t) = \begin{pmatrix} w_1*p^1 \\ w_2*p^2 \\ \cdot \\ \cdot \\ w_M*p^M \end{pmatrix},$$

and where weighting factors $w_i$ have been applied to the i-th row of the matrix A and of the vector $\vec{y}$. Each weighting factor is chosen to be positive, and the sum of the weighting factors over all tubes can be normalized to unity, without loss of generality. The unknown in the above is the two-component vector $\vec{x}(t)$ that quantifies the source/microphone circuit parameters in the time domain, in this case, the incident pressure $p^0(t)$ and source reflectance $r^0(t)$.

The choice of weighting factors in each calibration waveguide is guided by the same factors discussed earlier—they can weight in terms of the level of the pressure response waveform or amplitude envelope, a linear response function of calculated from the model, or a combination of the two.

Equations (63)–(64) form an overdetermined matrix system of equations when M>2, and there exists no unique solution for the unknown vector $\vec{x}$ that minimizes the following norm:

$$\|A*\vec{x} - \vec{y}\|. \tag{65}$$

As in the frequency-domain case, the matrix equation is unstable if the singular values of the matrix A decay gradually to zero or if the ratio between the largest and smallest non-zero singular values becomes too large. If the matrix equation is not unstable, then it is stable, and the corresponding method of solution can be reduced to matrix form. The associate set of regularization methods is to calculate the vector $\vec{x}$ that minimizes the above norm subject to the side constraint the minimizes the norm $$\|L*(\vec{x} - \vec{x}^\dagger)\|, \tag{66}$$

based upon an initial estimate $\vec{x}^\dagger$. The matrix L is selected, with typical selections being the identity matrix, and finite-difference approximations to the first or second derivative operator. Any of the direct and indirect regularization methods discussed earlier may be applied to solving this set of equations in the time domain, once it is shown that equations (65)–(66) can be expressed in terms of matrix multiplication. This regularization may be applied to the case M=2 as well.

Each element of the matrix is a time series, for example, the element in row i and column j is the time series $A_{ij}(t)$, which, in a discrete-time formulation, becomes a vector whose m-th element at the m-th time step is $A_{ij}[m]$. The square brackets [. . .] denotes the discrete time index. There are N time steps in the measured waveforms with the index m ranging from 0 to N–1. Similarly, the j-th element of the vector $\vec{x}$, denoted $x_j(t)$, is also a time series. Its m-th element at the m-th time step is $x_j[m]$. The convolution for the i-th row of the matrix A at an arbitrary time step n, for $0 \leq n \leq N-1$, is $$(A_{ij}*x_j)[n] = \sum_{m=0}^{n} A_{ij}[n-m]x_j[m]. \tag{67}$$

It is well known that the above equation may be expressed as the multiplication of a N×N matrix and a N×1 vector. The matrix value in row (n+1) and column (m+1) is $A_{ij}[n-m]$, and vector value in column (m+1) is $x_j[m]$.

An alternative formulation, the Pseudoinverse Deconvolution technique, is more explicit, which is based upon the analog of the deconvolution solution in the time domain to the pseudoinverse solution of a matrix set of equations in the frequency domain. The system of equations in the frequency domain, analogous to the time-domain system in equation (63) is $A\vec{x} = \vec{y}$, given in equation (55).

The pseudoinverse solution in the frequency domain is $$\vec{\tilde{x}} = (\tilde{A}A)^{-1}\tilde{A}\vec{y}, \tag{68}$$

where $\tilde{A}$ is the transpose matrix to A. With so-called Tikhonov regularization, the matrix $\tilde{A}A$ is replaced by $\tilde{A}A + \epsilon^2 \tilde{L}L$, where the regularization matrix L is arbitrarily chosen (one choice is the identity matrix), as discussed above, and where $\epsilon^2 \ll 1$.

In the time domain, the matrix inverse in the above is replaced by deconvolution. Each side of equation (63) is convolved with the transpose matrix $\tilde{A}$ of A defined in equation (64):

$$(\tilde{A}*A)*\vec{x} = \tilde{A}\vec{y}. \tag{69}$$

This system of equations is expressed in simplified notation by $$B^* \vec{x} = \vec{g}, \quad (70)$$

with the definitions $$B = \tilde{A}^* A, \quad \vec{g} = \tilde{A}^* \vec{y}. \quad (71)$$

Equation (70) in component form is $$B_{11}*p^0 + B_{12}*r^0 = g_1, \quad B_{21}*p^0 + B_{22}*r^0 = g_2. \quad (72)$$

By further manipulations, these equations can be written as a pair of equations involving $p^0$ and $r^0$ separately:

$$\Delta * p^0 = B_{22}*g_1 - B_{12}*g_2, \quad \Delta * r^0 = -B_{21}*g_1 + B_{11}*g_2, \quad (73)$$

where $$\Delta = B_{11}*B_{22} - B_{12}*B_{21}. \quad (74)$$

The time series $\Delta(t)$ plays the role of the determinant. Rather than explicitly solving for $p^0$ and $r^0$ in equation (73) by deconvolution, the reflectance circuit equation for the ear measurement is introduced as follows:

$$(\delta + r)*p^0 + r*p*r^0 = p. \quad (75)$$

Convolving the above equation with $\Delta$ and grouping terms proportional to the ear-canal reflectance r leads to $$\Delta*p - \Delta*p^0 = r*\{(\Delta*p^0) + p*(\Delta*r^0)\} \quad (76)$$

This is an equation of the form $$s = q *r \quad (77)$$

where $$q = (\Delta * p^0) + p*(\Delta*r^0), \quad s = (\Delta*p) - (\Delta*p^0), \quad (78)$$

and where equation (73) is substituted into the above. The unknown ear-canal reflectance is solved by deconvolution of equation (77).

The theory beginning with equation (69) can be developed in an equivalent manner using the Tikhonov regularization, such that the matrix B in the first equations (71) is re-defined to be $B = \tilde{A}^*A + \epsilon^2 \tilde{L}^* L$ in terms of the arbitrary matrix L. The initial time-domain formulation based upon equations (66)–(67) can be manipulated in similar fashion so that the unknown ear-canal reflectance is calculated using a single deconvolution.

The length optimization carried out in the time domain is generally similar to that in the frequency domain. As discussed at the end of Technique III, the preferred embodiment is to optimize lengths in the frequency domain, whether the ear-canal reflectance is calculated in the time or frequency domain.

Time-stretching of the stimulus may be applied in Technique IV. The responses in the calibration waveguides and the ear may optionally be time-compressed using the inverse allpass filter as discussed earlier. The difference in Technique IV is that it is not necessary that any of the time-compressed responses in one or more of the calibration waveguides be separable.

Figure 8:
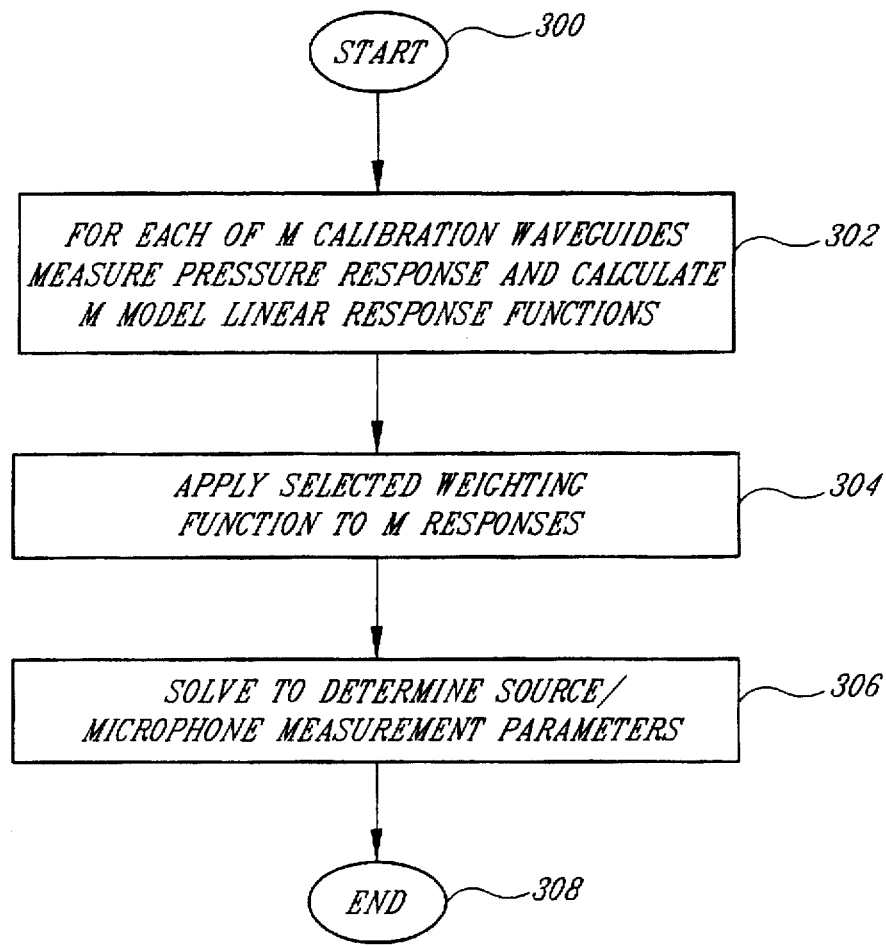
FIG. 8 is a flowchart of the calibration procedure used by the system of FIG. 1 with a plurality of acoustic calibration waveguides.

The operation of the system 10 for Techniques III and IV is illustrated in the flowchart of FIG. 8 where at a start 300, the characteristics of the measurement system 57 (see FIG. 1) have not yet been determined. In step 302, the user inserts the probe assembly 50 (see FIG. 2) in each of M calibration waveguides 60, delivers the excitation signal and collects a time-averaged response in each of the M calibration waveguides. As previously described, in Technique III the incident and first reflected signal must be separable in at least one of the M calibration waveguides. However, this condition of separability is not imposed on the system using Technique IV. The system 10 calculates M linear response functions based on measured responses from the M calibration waveguides. In step 304, the system 10 applies the selected weighting function to the responses for each of the M calibration waveguides. As discussed above, a plurality of different weighting functions may be applied. In step 306, the system 10 determines the source/microphone measurement parameters based on the M weighted responses. If Technique IV is used, this involves the solution of the overdetermined matrix, as described above. The system 10 ends the calibration measurement process at 308. The system 10 performs the steps outlined above with respect to FIG. 6 to determine the linear response function of the ear, or other unknown system. For the sake of brevity, those steps will not be repeated.

Summary of Linear Response Techniques

The system 10 has been described above for four different linear measurement techniques. The system 10 uses the customized stimulus signal to produce a well defined acoustic stimulus and the calibration information derived from one or more calibration waveguides 60 to characterize the probe assembly 50 and its components. This information is used to determine acoustic response functions of the unknown system such as the impulse response, reflection coefficient, and other related acoustic responses in terms of the reflection function. Analyses of these acoustic response functions provides clinically important information about the state of the middle ear.

Signal processing algorithms well known in the art, such as Fourier analysis, are used to combine this acoustic response information with OAE measurements to obtain a power transfer characterization of the unknown system, as described later. Whether alone or in combination with other measurements, the acoustic response measurement provides the basis for the practical application of a computer-based hearing assessment device for humans, but also for use in animal tests. Early detection of hearing abnormalities has recently become an established health care priority. The system 10 is particularly valuable for use in testing neonates and young infants.

Static Pressurization

The system 10 may be generalized by applying an excess positive or negative static pressure to the ear canal, as is typical of tympanometry systems. Such static pressure may also be applied to the calibration-tube response measurements using the pump 68 (see FIG. 2) to vary the static pressure in a manner well-known in tympanometry systems. Thus, the response may be obtained as a dual function of static pressure and frequency, or static pressure and time. This representation is a generalization of traditional single-frequency or multi-frequency tympanometry. As such, the reflectance can be represented as a dual function of static pressure and frequency both in system 10, but also in any conventional system of single-frequency or multi-frequency tympanometry that measures a complex admittance or impedance.

The standard response function in tympanometry is acoustic admittance $Y(f, P_s)$, defined as a function of frequency $f$ and static pressure $P_s$. Early tympanometers measured only the magnitude of the admittance, and later tympanometers were phase-sensitive (i.e., they measured both the magnitude and phase, or, equivalently, the real and imaginary parts, of the admittance). The so-called reflectance tympanogram can be defined for any tympanometric measurement system that measures a phase-sensitive response function of the ear, in particular, the magnitude and phase of the admittance.

This reflection coefficient $R(f,P_s)$ at frequency $f$ and static pressure $P_s$ is calculated from the admittance $Y(f,P_s)$ measured in any tympanogram and the characteristic impedance $Z_c$ at the entryway of the ear by $$R(f, P_s) = \frac{1 - Z_c Y(f, P_s)}{1 + Z_c Y(f, P_s)}, \quad (79)$$

where the characteristic impedance $Z_c = \rho c/S$, such that the equilibrium density of air is $\rho$, the phase velocity of sound is c, and the cross-sectional ear of the ear canal at the probe assembly of the tympanometer is S. The frequency variation in $Z_c$ may be neglected. Because the range of static pressures is negligible compared to atmospheric pressure, the static-pressure variation in $Z_c$ may also be neglected. The (energy) reflectance tympanogram is a plot of $|R(f,P_s)|^2$ versus static pressure or frequency. Other representations of reflection coefficient magnitude, phase, real and imaginary parts, and group delay may also be plotted as functions of static pressure and frequency. It is a real quantity that varies between zero and unity.

The ear-canal area can be measured, estimated from probe size or other subject data, including weight, gender and age. It can be estimated acoustically using a wideband measurement of acoustic resistance. The reflectance is insensitive to small errors in measuring the cross-sectional area of the ear canal, and such small errors have little effect as static pressure is varied. The reflectance tympanogram provides additional information about the tympanogram that may be useful in assessing neonatal tympanograms, which are difficult to interpret for infants younger than 3-months-old.

The reflectance tympanogram directly quantifies the relative accuracy of the assumption underlying tympanometry, namely, that there is no energy transmitted into the middle and inner ear at the largest positive and largest negative static pressures. It follows from this assumption that the energy reflectance should equal unity at these extreme static pressures. It has been unrecognized that this is testable for an individual tympanogram by direct evaluation of the reflectance. Values of the reflectance less than unity indicate energy transmission into the middle ear, viscothermal wall losses at the ear canal that tend to be small, and the possible existence of additional wall loss mechanisms, particularly in neonates.

Figure 7:
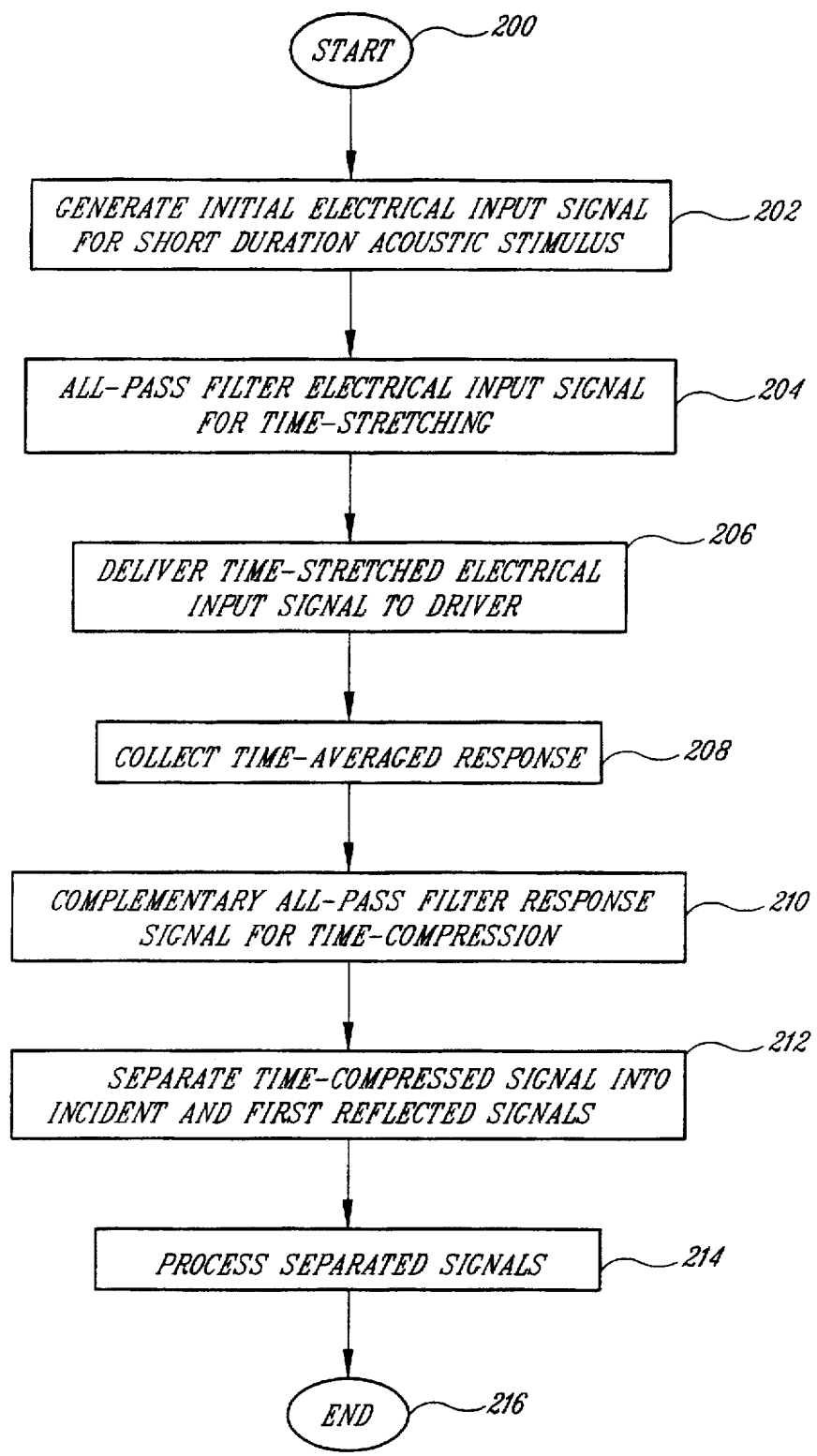
FIG. 7 is a flowchart of the time-stretching and compression measurements used by the system of FIG. 1.
Figure 9:
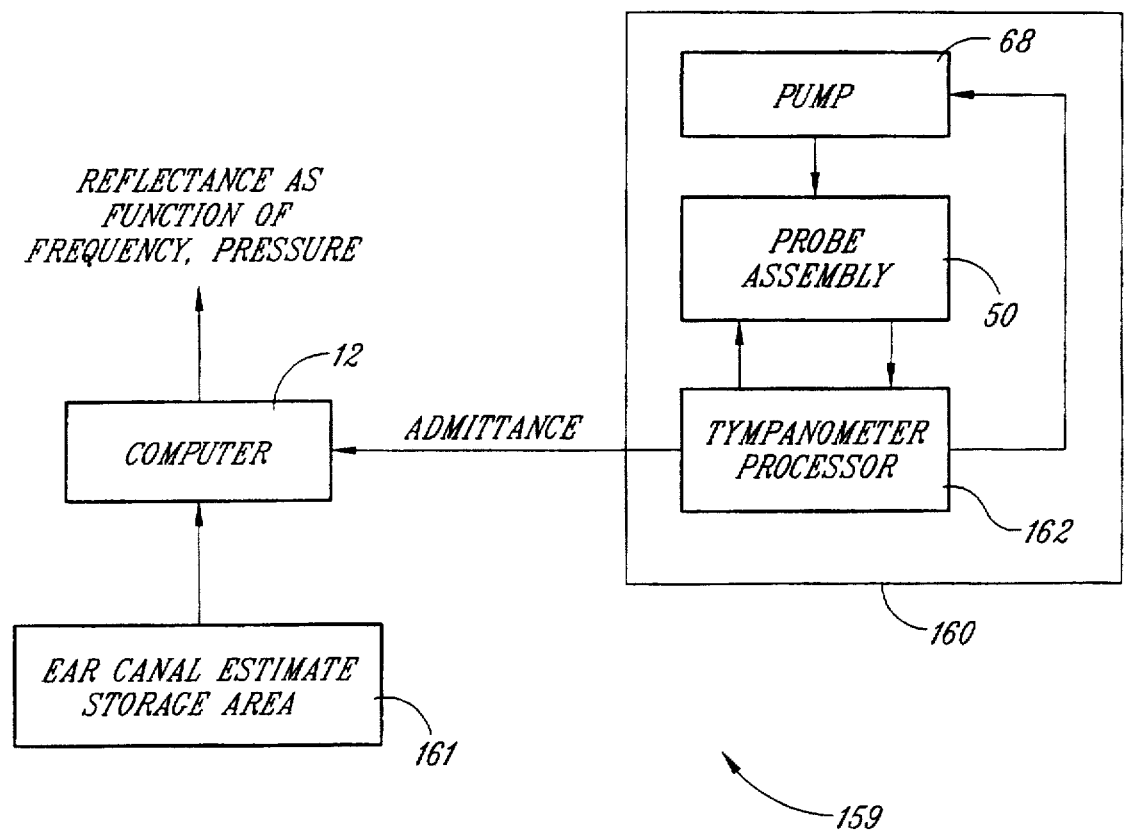
FIG. 9 is a functional block diagram of the inventive system to measure a reflectance tympanogram.

FIG. 9 is a functional block diagram illustrating the system for the measurement of a reflectance tympanogram. Many of the components illustrated in FIG. 9 have been previously described, and will not be described in further detail herein. The system 159 includes the computer 12 (see FIG. 1) and probe assembly 50 (see FIG. 2) which have been previously described. In addition, the system 159 includes a conventional tympanometer 160 which measures admittance as a function of static pressure. Thus, the pump 68 is illustrated in FIG. 7 in part of the tympanometer 160. In a preferred embodiment, a tympanometer processor 162 generates the electrical signals for the probe assembly 50. However, the computer 12 can also generate signals to measure the admittance. In addition, the tympanometer 160 controls the static pressure set by the pump 68. In the presently preferred embodiment, a tympanometer processor 162 utilizes the probe assembly 50 to perform the admittance measurement. The admittance data generated by the tympanometer 160 are coupled to the computer 12. In addition, the computer 12 receives an ear canal area estimate 161, which can be estimated in the manner described above. The computer 12 uses the ear canal area estimate 161 and the admittance generated by the tympanometer 160 to calculate reflectance as a function of frequency and pressure using equation (79) above.

Power delivered to the ear: Linear response

As previously discussed, the term linear response function refers to a power-based description of the acoustic response of the ear. As described earlier, such a linear response function is invariant to changes in stimulus level, as long as both the measurement system and the auditory system behaves linearly. This is in contrast to the acoustic pressure response of the ear, which increase linearly with stimulus level in an ideal linear system. The other part of the definition of linear response function states that it is power-based, which means that the power delivered from the acoustic source to the ear may be calculated. This is also in contrast to the acoustic pressure response of the ear, which cannot, by itself, be used to calculate the delivered power. As discussed by D.H. Keefe et al., "Ear-canal impedance and reflection coefficient in human infants and adults," J. Acoust. Soc. Am. 94:2617–2638, 1993, the power absorbed by the ear is closely connected with the structure of the pure-tone threshold of audibility, and it can be appreciated that measurements of power absorbed in normal and impaired-hearing populations may be useful in understanding the influence of conductive and cochlear impairments on the pure-tone audiogram.

Before defining and discussing the nonlinear response attributes of the ear (or any other substantively one-dimensional acoustic system of interest), the power delivered by a source to the ear is expressed using the reflectance, admittance and impedance representations of an ideal system whose response is linear.

The reflectance representation is appropriate to the ideal case where the source is coupled to the load, i.e., the ear canal, by a long cylindrical tube with rigid walls, in which viscothermal losses are neglected. An acoustic source creates an incident pressure signal $P_i(f)$. Its corresponding power variable is the incident acoustic intensity $I_i(f)$, which is the energy per unit time and per unit area in the traveling wave, given by $$I_i(f) = \frac{1}{2} \frac{|P_i|^2}{\rho c} \quad (80)$$

The integral of this acoustic intensity over the cross-sectional area of the cylindrical tube, which in this case of loss-free, one-dimensional propagation is simply the product of the intensity and the area, is the acoustic power in the incident wave. The unknown load acts as a discontinuity, creating a reflected wave back down the cylindrical tube, and a combination of absorbed and transmitted waves within the unknown load. The so-called energy reflectance, which may also be called a power reflectance, is the ratio of the reflected acoustic intensity traveling back down the tube to the incident acoustic intensity. Since the reflected power is also the product of the reflected acoustic intensity and the cylindrical tube area, then the energy reflectance is the ratio of reflected acoustic power to incident acoustic power.

If the frequency-domain pressure of the incident wave is $P_i(f)$, and the pressure of the reflected wave is $P_r(f)$, then the pressure reflectance (i.e., the pressure reflection coefficient) $R(f)$ is defined by $$R(f) = \frac{P_r(f)}{P_i(f)}. \tag{81}$$

Since the pressures are represented by complex quantities, the pressure reflectance is, in general, also complex, and can be written as $$R(f) = |R(f)| e^{j\Phi(f)}, \tag{82}$$

where $j=\sqrt{-1}$. In contrast, the energy reflectance is a real quantity, because it is a ratio between two types of energy flux, or two types of power. The energy reflectance as defined above is equal in the frequency domain to the complex squared magnitude of the pressure reflectance, $|R(f)|^2$. The phase angle $\Phi(f)$ of the pressure reflectance quantifies the phase difference between the reflected and incident pressure waves.

As long as the ear canal is approximately cylindrical in shape and that ear-canal loses are negligible, the energy reflectance and the magnitude of the pressure reflectance are independent of the probe assembly position within the ear canal. In this idealized measurement, the long cylindrical tube coupling the source to the ear canal has been constructed so that there is a match between its area and the ear-canal area. If there is a step change in area, then there is an additional reflection at the end of the cylindrical tube that must be accounted for. In the practical measurement Technique Numbers I-IV, the calibration step enables the measurement of reflectance (and other linear response functions) without coupling a long cylindrical tube to the ear canal.

The phase of the pressure reflectance varies with probe position. It is convenient to define the group delay $\tau$ associated with the phase by $$\tau = -\frac{1}{2\pi} \frac{d\Phi}{df}, \tag{83}$$

which measures the delay associated with the reflection of energy, dependent upon middle-ear factors as well as the round-trip travel time from the eardrum to the probe assembly. In the absence of ear-canal losses, if the probe assembly is placed a short distance $\Delta L$ further from the eardrum, the group delay increases by $(2\Delta L/c)$.

It follows from the law of energy conservation that the total power $\mathring{A}_a(f)$ absorbed by the ear can be measured as the difference between the incident and reflected power. It follows that the total power delivered to the ear is $$\Pi_a(f) = (1-|R(f)|^2)\frac{1}{2}\frac{S|P_i|^2}{\rho c} \tag{84}$$

This expression for power has the disadvantage that it is not directly expressed in terms of a linear response function and a directly measurable acoustic quantity in the ear canal. That is, it is the total pressure that is measured in the ear rather than the incident pressure.

The independence of energy reflectance on probe-assembly position makes it an attractive linear response function of the ear. This is in contrast to the impedance and admittance measured in the ear canal, which vary according to the location of the probe assembly. Nevertheless, the admittance representation has its advantages. The acoustic admittance $Y(f)$ has been defined as the volume-flow response to an incident pressure excitation at a particular frequency $f$, namely, $$Y(f)=U(f)/P(f), \tag{85}$$

where $P(f)$ is the total pressure measured at by the probe assembly microphone and $U(f)$ is the volume flow injected by the acoustic source into the ear canal. It is a complex quantity which is expressed in rectangular form below:

$$Y(f)=G(f)+jB(f). \tag{86}$$

The real part of the admittance is the conductance $G(f)$, and the imaginary part of the admittance is the substance $B(f)$.

The acoustic impedance $Z(f)$ has been defined as the pressure response to an incident volume flow excitation at a particular frequency, namely, $$Z(f)=P(f)/U(f). \tag{87}$$

It is a complex quantity which is expressed in rectangular form below:

$$Z(f)=R(f)+jX(f). \tag{88}$$

The real part of the impedance is the resistance $R(f)$, and the imaginary part of the impedance is the reactance $X(f)$.

The power delivered to the ear may be expressed in term of the conductance and the squared pressure, or the resistance and the squared volume as follows:

$$\begin{aligned}\Pi_a &= \frac{1}{2} G|P(f)|^2. \\ &= \frac{1}{2} R|U(f)|^2.\end{aligned} \tag{89}$$

Even though the conductance and the resistance vary with the position of the probe assembly, they may be used to calculate the power. In particular, the top relation (conductance-power) of equation (89) is advantageous, because the unknowns are the conductance, the particular linear response function chosen, and the squared magnitude of the total microphone pressure measured by the probe.

No matter which of the equations for sound power is used (equations (84) or (89)), the results are precisely identical. This completes the summary of power transfer in an ideal linear system.

Power delivered to the ear: Nonlinear responses

The acoustic response of the ear to stimuli presented in the ear canal contains both linear and nonlinear response attributes, and it is desirable to measure the nonlinear response characteristics of the ear for moderate excitation pressure levels, approximately 0–80 dB SPL. It is well known that the evoked nonlinear response of the cochlea is particularly important for low-level sounds, and the magnitude of the nonlinear response saturates at excitation pressure levels of approximately 40 dB SPL in the ear canal. These evoked, nonlinear, ear-canal pressure responses are called evoked otoacoustic emissions (OAEs), and are classified according to the nature of the stimulus that evokes the OAE. Major classes include transient-evoked otoacoustics emissions (TEOAE), with click-evoked otoacoustic emissions (CEOAE) as a prominent example, and distortion-product otoacoustic emissions (DPOAE).

TEOAEs employ a transient stimulus such as that used in measuring linear response functions of the ear. Transient stimuli have include clicks, chirps and tone-bursts among others. DPOAEs employ a continuous tone stimulus such as has also been used in measuring linear response functions of the ear. The continuous stimulus in a linear response measurement is comprised of a single frequency for which the response is measured, and the frequency is subsequently varied to obtain responses across the desired bandwidth. However, the continuous stimulus in a DPOAE measurement is comprised of two frequencies $f_1$ and $f_2$, and the response is measured at one or more separate frequencies, for example, $2f_1-f_2$. Thus, DPOAE measurements are inherently different at the stimulus-design level from continuous-tone linear response measurements, whereas TEOAE measurements are not different from transient linear response measurements.

Typically, the TEOAE response is time-averaged over a number of presentations of the transient stimulus, and the DPOAE response is time-averaged over a long duration of the continuously presented stimulus. Either type of averaging allows extraction of the OAE response from the background random noise. However, this does not allow extraction of the distortion associated with the probe assembly and measurement system from the OAE response of the ear. This is because the distortion, if present, is coherent with the stimulus and is not reduced by signal averaging.

Because the iso-level Techniques I–IV use transient stimuli, particular attention is devoted herein to TEOAE techniques. Some TEOAE measurement techniques (the click-evoked response is used as a typical example) use an iso-level stimulus, for example, a click at a fixed level is presented and the CEOAE response measured. D. T. Kemp, "Stimulated acoustic emissions from within the human auditory system," *J. Acoust. Soc. Am* 64:1386–1391, 1978. Such iso-level CEOAE techniques utilize time gating, such that the initial portion (typically, 2.5–5 ms) of the response after presentation of the click is nulled. In part, this is because the response of the middle ear dominates the CEOAE during the initial 2 ms or so, with an amplitude that is approximate 30 times larger than the subsequent amplitude of the CEOAE.

Some prior art references have stated that the resulting CEOAE response in a particular range of time delays is due entirely to a reflection from the cochlea, so much so that a CEOAE is often called a cochlear echo. For example, the CEOAE is described in U.S. Pat. No. 4,374,526, issued to D. T. Kemp in 1983, as "substantially exclusively only said inner ear reflection." In yet another reference, U.S. Pat. No. 3,294,193, to J. F. Zwislocki, it is stated that the measurement of the impedance of the ear depends on the acoustic conditions encountered at the external ear, middle ear and cochlea (inner ear). This impedance evaluated just in front of the eardrum is the middle ear impedance. In the frequency bandwidth important to speech communication (the mid kilohertz range), "It appears, then, that by good design in the very frequency range that is most important for communication, the middle ear simply reflects the input properties of the cochlea . . . " P. Dallos, "The Auditory Periphery," Academic Press, U.S.A., p. 112, 1973. Thus, the middle-ear impedance evaluated in the mid-frequency range also measures, substantially exclusively, the reflection from the cochlea. Moreover, the reverse transmission of the CEOAE signal from the cochlea to the ear canal involves the response of the middle ear, eardrum and external ear canal. The evoked OAE depends upon the external ear canal response through the influence of standing waves in the ear canal. J. H. Siegel, "Ear-canal standing waves and high-frequency sound calibration using otoacoustic emission probes," *J. Acoust. Soc. Am.* 95:2589–2597, 1994. The existence of such standing waves is precisely why the acoustic impedance is calculated just in front of the eardrum in order to remove such effects.

An inherent difference between evoked OAEs and iso-level response measurements of the ear such as impedance, is that the evoked OAE is highly nonlinear whereas practical impedance measurements of the ear have been interpreted by assuming that the ear responds linearly. This approximation of linearity is known to be highly accurate for the external and middle ear over the range of moderate excitation levels that are relevant, except for the behavior of the middle-ear reflex. The action of the middle-ear reflex is initiated by the onset of an acoustic stimulus, and the middle ear behaves in a linear fashion after the reflex has been initiated. The existence of evoked OAEs makes the approximation of linearity of the cochlea highly suspect for acoustic impedance measurements in the mid-frequency range. But first, TEOAE measurement techniques are described that take account of their nonlinear response.

Some TEOAE techniques use multi-level stimuli, and the TEOAE response is extracted from a differential combination of the responses to each of the stimuli. For example, the "nonlinear balance" technique presents a single click of positive polarity and three clicks of negative polarity and one-third the amplitude of the initial click. The response to each of the four clicks is summed to form the nonlinearly balanced CEOAE response. D. T. Kemp et al., "Acoustic emission cochleography-Practical aspects," *Scand. Audio. Suppl.* 25:71–95, 1986. This differential CEOAE eliminates the pressure response of the ear that is linearly proportional to stimulus level. Since the middle ear response dominates the first 2 ms of the response, and since the middle ear response is linear, then it might be expected that this nonlinear balance technique would enable measurement of CEOAE during this initial range of time latencies. Such is not the case due to the presence of nonlinear distortion in the probe assembly and measurement system. Thus, time gating over the initial 2.5–5 ms of the CEOAE measurement is used in methods based upon nonlinear balance and related subtraction methods in the prior art. D. T. Kemp et al., "Acoustic emission cochleography-Practical aspects," *Scand. Audio. Suppl.* 25:71–95, 1986.

The existence of TEOAEs that are dependent upon stimulus level demonstrates that the acoustic impedance should also be nonlinear. While the external- and middle-ear responses are linear, the cochlea response is nonlinear. Since the acoustic middle ear impedance is dominated by the cochlear response at mid-frequencies, it is anticipated that this impedance is nonlinear in this frequency range. Since the level of TEOAEs is much smaller than the stimulus level in the ear canal, it is also anticipated that the nonlinear component to the impedance is much smaller than the linear component. This nonlinear component of the impedance has been measured. D. Jurzitza and W. Hemmert, "Quantitative measurements of simultaneous evoked otoacoustic emissions," *Acustica* 77:93–99, 1992.

It can be appreciated that a technique to measure the nonlinear power-based transfer function of the ear, i.e., its nonlinear transfer function, may be useful in understanding clinical pathologies of the ear, because there exists no single technique that can differentially diagnose conductive pathologies associated with the middle ear from sensorineural pathologies associated with the cochlea. The iso-level component of the impedance or other transfer function describes the conductive pathway into the middle ear. Whereas the input impedance of the middle ear of a healthy subject is dominated by the cochlear response, the same response function for a subject with a conductive impairment may have a quite different response pattern. The nonlinear component of the impedance or other power-based response function measured at various stimulus levels is strongly influenced by the nonlinear cochlear response. This suggests that a simple technique for measurements of one or more nonlinear transfer functions of the ear may have clinical applications.

The nonlinear measurement technique is a generalization to multiple stimulus levels of the iso-level response techniques. Thus, these nonlinear measurement techniques include the iso-level response of the ear at a reference stimulus level as a particular case. The specific nonlinear measurement techniques of interest include multi-level generalizations of the iso-level Technique Numbers I–IV and the iso-level technique for measuring impedance and reflectance discussed in D. H. Keefe, *J. Acoust. Soc. Am.* 91:470–485, 1992. This latter method adapted and simplified an impedance measurement technique used in measuring the acoustic impedance in the ears of cats, as discussed in J. B. Allen, (Springer-Verlag, N.Y.) eds. J. Allen, J. Hall, A. Hubbard, S. Neely and A. Tubis, 1985) so that it could be used in human ears from adults to neonates, and enable the measurement of reflectance as well. This technique has subsequently been further applied to measurements in adults and infants, as discussed in D. H. Keefe et al., *J. Acoust. Soc. Am.* 94:2617–2638, 1993, and replicated in adults, as discussed in S. E. Voss and J. B. Allen, "Measurement of acoustic impedance and reflectance in the human ear canal," *J. Acoust. Soc. Am.* 95:372:384, 1994.

A particular stimulus level is chosen, and the iso-level calibration of the system is carried out for the particular technique chosen. Then, the next stimulus level is chosen, and another iso-level calibration is carried out. These steps are performed for all the desired stimulus levels in the dynamic range of the measurement. The probe assembly is inserted into the ear canal, and the pressure responses are measured using the identical set of stimuli at their various levels. For any given stimulus level, the iso-level transfer function is calculated in the time or frequency domain. The result is a measurement of the transfer function across a plurality of stimulus levels. In these nonlinear measurement techniques, there is no use of time gating of the measured pressure response in the ear.

A "differential nonlinear transfer function" may also be defined by subtracting the transfer function measured at one stimulus level from that measured at some other stimulus level. For example, the differential impedance, differential reflectance, and differential admittance may be calculated as a function of frequency, stimulus level, and, optionally, static pressure in the ear canal. For example, the differential impedance or energy reflectance may be calculated as a function of both frequency and level. Yet another alternative is to measure the power in the response by using any of the above expressions for power delivered to the ear as a function of stimulus level. In the absence of all nonlinearities, changing the stimulus waveform amplitude by a factor $\beta$ changes the absorbed power by $\beta^2$. Suppose the power-based response and ear-canal pressure are measured at a stimulus amplitude of unit (in arbitrary units) and at a stimulus amplitude of $\beta$ times unity.

The power absorbed by the ear in the first case is $\mathring{A}_a(f,1)$, and in the second case is $\mathring{A}_a(f,\beta)$. The differential nonlinear power $\Delta\mathring{A}_a(f,\beta,1)$ absorbed by the ear is defined by $$\Delta\mathring{A}_a(f,\beta,1) = \mathring{A}_a(f,\beta) - \beta^2 \mathring{A}_a(f,1) \tag{90}$$

The differential nonlinear power absorbed by the ear is equal to zero in the absence of nonlinearities. It is straightforward to define equivalent measures of nonlinear power such as the relative change in the differential nonlinear power, by forming such quantities as $\Delta\mathring{A}_a(f,\beta,1)/\mathring{A}_a(f,\beta)$. It is also straightforward to measure the differential nonlinear power absorbed by the ear as static pressure is varied in the ear canal.

To summarize, the nonlinear response of the ear is measured using four sets of nonlinear responses: (1) a nonlinear transfer function, (2) a differential nonlinear transfer function, (3) power absorbed by the ear as a function of stimulus level, and (4) differential nonlinear power absorbed by the ear. The invention extends to the multi-level generalization of the iso-level Techniques I–IV described earlier and the iso-level impedance/reflectance technique of D. H. Keefe, *J. Acoust. Soc. Am.* 91:470–485, 1992, which can also obviously be used for admittance measurements since admittance is the inverse of impedance. The power absorbed by the ear as a function of stimulus level, and the differential nonlinear power absorbed by the ear, are defined by any technique that measures power as a function of stimulus level.

In the general case, the power absorbed by the ear for each stimulus level might be measured in terms of a stored parameter model of the measurement system, including the measurement system parameters, which are determined at the factory or elsewhere. The user simply inserts the probe assembly into the ear, delivers an acoustic stimulus at a particular level, and measures the pressure response at the probe microphone. This pressure response is used with the stored model to calculate each transfer function, which is used with the measured pressure response in the ear to calculate power absorbed. These steps are carried out for as many different stimulus levels as is desired.

Alternatively, there might exist one or more calibration waveguides in which the user inserts the probe, delivers an acoustic stimulus at one or more stimulus levels, and measures the corresponding pressure responses. These pressure responses might be compared with one or more stored calibration responses and one or more stored calibration models, such that a sufficiently good agreement between the measured and stored responses would check that the one or more stored calibration models could be used with the measured response in the ear to calculate the power absorbed by the ear at each stimulus level.

Elaborating the above alternative, the transfer function of each calibration waveguide might be predicted from a calibration model, and used with the measured pressure responses in each calibration waveguide to calculate the equivalent circuit parameters (Reflectance, Thevenin or Norton) of the source, microphone and related instrumentation in the measurement system. Finally, this calibration model might include viscothermal losses in the calibration waveguide, which includes as particular examples the iso-level approaches in Techniques I–IV, and the iso-level techniques of Allen (1986), Keefe et al. (1992), and Voss and Allen (1994). In each alternative, the power absorbed by the ear as a function of stimulus level, and the differential nonlinear power absorbed by the ear, are calculated from the measured transfer functions of the ear and the measured pressure responses in the ear.

The interpretation of any of these nonlinear-power techniques depends upon the categorization of a response into ear-nonlinearity or measurement-nonlinearity. The ear-nonlinearity is what any of these procedures is designed to measure, but nonlinearity in any component of the measurement system is a confounding factor.

One procedure to test whether the measurement nonlinearity is indeed negligible for a given nonlinear transfer function is to compare the set of transfer functions and the set of pressure response measured in one or more of the calibration tubes with the sets measured in the ear. Alternatively, the set of transfer functions and set of pressure responses is measured at a plurality of stimulus levels in a coupler whose response is linear, and whose transfer function, e.g., its impedance, is similar, in the absence of nonlinear effects, to that of the ear under test. Alternatively, the power-based response and the pressure response is measured in a coupler whose response is linear, and whose linear power-based response (for example, impedance) is similar to that of the ear under test. Probe distortion in the acoustic source is an important contributor to measurement-nonlinearity, and its distortion characteristics are controlled by using the same stimulus level and driving a coupler whose impedance is as close as possible to the ear under test. The probe distortion is negligibly affected by the evoked OAE from the ear, so that it is the impedance measured at moderate stimulus levels that is controlling the magnitude of the distortion.

The advantages of the use of a time-stretched stimulus such as a chirp, followed by time-compression of the pressure response, has been discussed with respect to the iso-level techniques. One advantage was that probe distortion associated with high peak amplitudes in the stimulus can be significantly reduced by time stretching, such that the total energy in the stimulus remains the same. This is even more important for the nonlinear power-based measurements, because probe distortion is a more significant confounding factor.

For such time-stretched stimuli, it would be meaningless to time gate the pressure response detected by the ear-canal microphone, because the duration of the time-stretched stimuli may exceed the duration of the time gate typically used in TEOAE measurements (i.e., nulling 2–5 ms). The time-stretched electrical stimulus, in general, continues generating an acoustic stimulus over longer durations. Alternatively, a much longer time gate would null out most of the time-stretched response. This shows that time gating of the microphone pressure response can play no role in the time-stretching/time-compression techniques described in this application.

Nevertheless, by time-stretching the stimulus, the overload of the acoustic source that would otherwise occur with click stimuli just after the onset of the click is significantly reduced. The relative reduction of probe distortion with differing amounts of time stretching is assessed by measurements in the calibration waveguides or other acoustic couplers described above.

Any of the nonlinear power-based measurements can be carried out a further generalization of the system, by applying an excess positive or negative static pressure. This has been described for the iso-level response function measurements. Any of the nonlinear responses (1)–(4) listed above may be measured as a function of static pressure in the ear canal, stimulus level, and time or frequency. When the static pressure in the ear canal is manipulated as an additional variable, the particular technique used to measure the iso-level transfer function of the ear is arbitrary. The preferred embodiment is in the frequency domain using one of the iso-level Techniques I–IV discussed above. Such power-based response functions as well as power $$\hat{A}_\omega(f, \beta, P_s)$$

delivered to the ear are obtained as functions of frequency (or time), stimulus amplitude $\beta$, and static pressure $P_s$ in the ear canal. These nonlinear measurements of power-based response functions and power are defined such that the choice of technique for measuring each iso-level power-based response function is arbitrary.

In the general case, each iso-level power-based response function, i.e., transfer function, might be measured in terms of a stored calibration model implemented at the factory or elsewhere, such that the user simply inserts the probe assembly into the ear, varies the static pressure, delivers an acoustic stimulus, and measures the pressure response at the probe microphone. This pressure response is used with the stored model to calculate each transfer function as a function of static pressure in the ear.

Alternatively, there might exist one or more calibration waveguides in which the user inserts the probe, varies static pressure, delivers an acoustic stimulus, and measures the pressure response. This pressure response might be compared with a stored calibration response and stored calibration model, such that a sufficiently good agreement between the measured and stored responses would check that the stored calibration model could be used with the measured pressure response in the ear to calculate each transfer function.

Elaborating the above alternative, the transfer function of each calibration waveguide might be predicted from a calibration model, and used to calculate the equivalent circuit parameters (reflectance, Thevenin or Norton) of the source, microphone and related instrumentation in the measurement system. Finally, this calibration model might include viscothermal losses in the calibration waveguide, but generalized to static pressurization and multiple stimulus levels.

It can be appreciated from the foregoing discussion that the power absorbed by the ear as a function of stimulus level, and the differential nonlinear power absorbed by the ear, can be calculated using any of these general alternatives as a function of static pressure using the set of measured pressure responses in the ear and set of measured transfer functions for a plurality of stimulus levels. The preferred embodiment is in the frequency domain using one of the iso-level Techniques I–IV discussed above.

Figure 10:
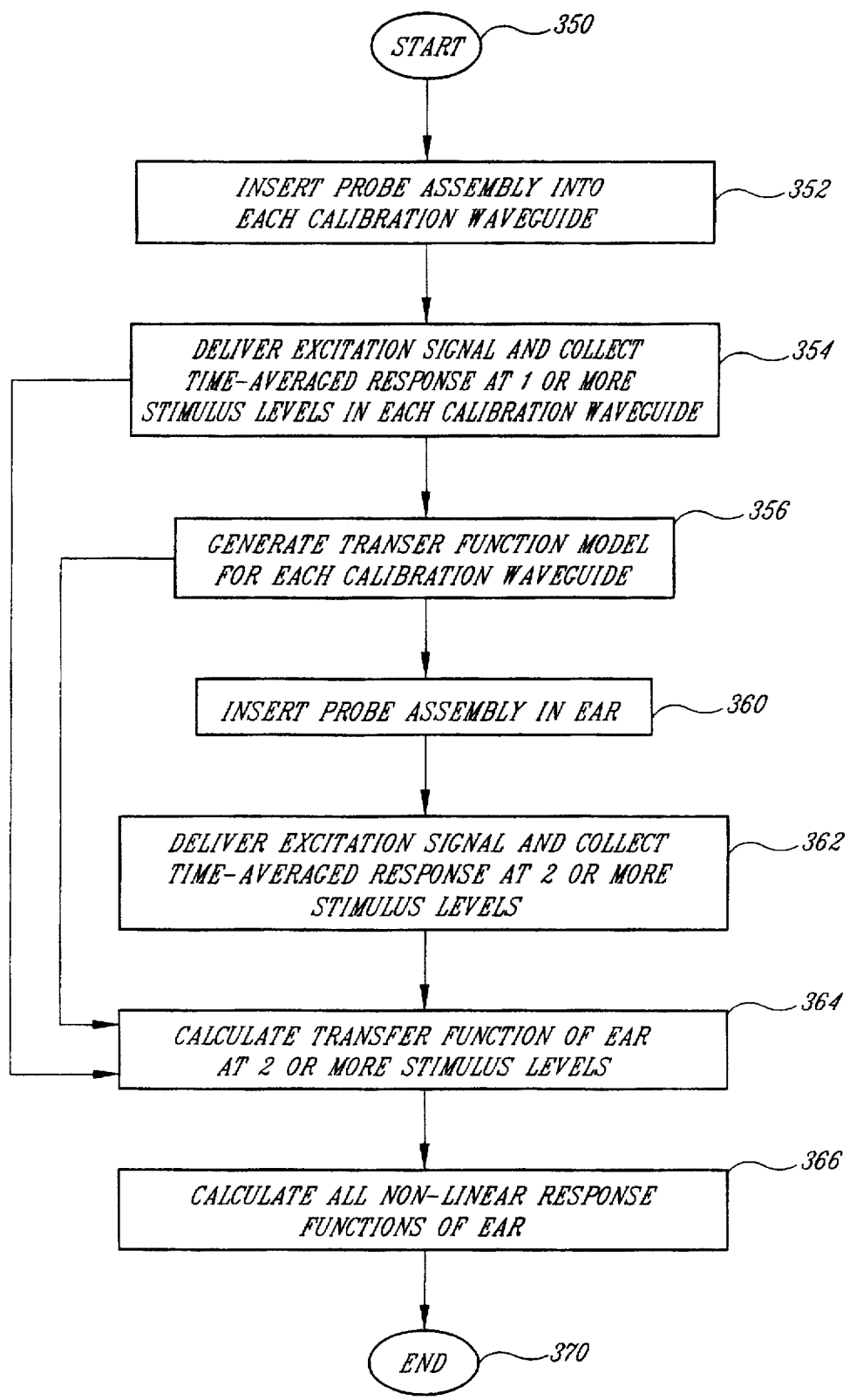
FIG. 10 is a flowchart of the nonlinear power-based response measurement procedure used by the system of FIG. 1.

The operation of the system 10 to determine a nonlinear acoustic transfer measurement is illustrated in the flowchart of FIG. 10. At a start 350, the transfer characteristics of the measurement system 57 (see FIG. 1) are unknown. In step 350, the user inserts the probe assembly 50 into each of the calibration waveguides 60. In step 354, the system 10 delivers an excitation signal and collects a time-averaged response at one or more stimulus levels in each of the calibration waveguides 60. In step 356, the system generates a model of the transfer function for each of the calibration waveguides 60 using the time-averaged responses collected in step 354.

To measure the nonlinear transfer function of the ear, the probe assembly 50 is inserted into the ear in step 360. In step 362, the system 10 delivers an excitation signal and collects a time-averaged response in the ear at two or more stimulus levels. It should be noted that, for the sake of accuracy, the stimulus levels presented to the ear are substantially equal to the stimulus levels presented to the calibration waveguides. For example, the system 10 can use two stimulus levels presented to the calibration waveguides in step 354, and use the same two stimulus levels presented to the ear in step 362. The use of the same stimulus levels during the calculation of the transfer function model serves to minimize the nonlinear effects of the measurement system 57. However, if the measurement system 57 is linear over the range of stimulus levels, the stimulus levels used in the calibration waveguides do not have to match the stimulus levels presented to the ear.

In step 364, the system 10 calculates the transfer function of the ear at the two or more stimulus levels using the time-averaged response signals collected from the calibration waveguides, the model transfer function for each of the calibration waveguides, and the time-averaged response from the ear. In step 366, the system 10 calculates all nonlinear transfer functions of the ear. The process terminates at an end 370.

It is to be understood that even though various embodiments and advantages of the present invention have been set forth in the foregoing description, the above disclosure is illustrative only, and changes may be made in detail, yet remain within the broad principles of the invention. Therefore, the present invention is to be limited only by the appended claims.

What is claimed is:

1. A system for the measurement of a linear response of the ear, the system comprising:

a probe assembly positionable in the ear;

an acoustic source within said probe assembly to produce an acoustic stimulus in response to an electrical input signal;

an acoustic energy detector within said probe assembly to detect acoustic energy signals and convert said detected acoustic energy signals to detected electrical signals;

one or more acoustic calibration waveguides, each having predetermined dimensions and having first and second ends;

a stimulus signal generator coupled to said acoustic source to generate said electrical input signal when said probe assembly is positioned in said first end of said one or more acoustic calibration waveguides, said stimulus signal generator also generating said electrical input signal when said probe assembly is positioned in the ear;

a signal processor receiving a set of detected calibration electrical signals from said acoustic energy detector when said probe assembly is positioned in each of said one or more acoustic calibration waveguides and receiving a detected measurement electrical signal when said probe assembly is positioned in the ear; and a computer processor containing a calibration waveguide model indicative of an acoustic transfer characteristic, including viscothermal effects, for each of said one or more acoustic calibration waveguides, said computer processor determining a linear response function of the ear based on said set of detected calibration electrical signals, detected measurement electrical signal and said calibration waveguide model.

2. The system of claim 1 wherein said linear response function of the ear includes a time-domain linear response function of the ear.

3. The system of claim 2 wherein said time-domain linear response function comprises a selected one of a set including a reflection function, a time-domain impedance function and a time-domain admittance function.

4. The system of claim 1 wherein said linear response function of the ear includes a frequency-domain linear response function of the ear.

5. The system of claim 4 wherein said frequency-domain linear response function comprises a selected one of a set including a reflection coefficient function, an impedance function, and an admittance function.

6. The system of claim 1 wherein said probe assembly substantially seals said one or more acoustic calibration waveguides and the ear from ambient atmosphere.

7. The system of claim 1 wherein said predetermined dimensions include an acoustic calibration waveguide length and a cross-sectional area as a function of position along said acoustic calibration waveguide for each of said one or more acoustic calibration waveguides.

8. The system of claim 7 wherein each of said one or more acoustic calibration waveguides is a cylindrical tube with said cross-sectional area having a constant value as a function of said position.

9. The system of claim 7 wherein said second end in each of said one or more acoustic calibration waveguides is terminated by an acoustic termination having known acoustic transfer characteristics to define said calibration waveguide model.

10. The system of claim 7 wherein said second end in each of said one or more acoustic calibration waveguides is a closed end.

11. The system of claim 7 wherein said second end in each of said one or more acoustic calibration waveguides is an open end.

12. The system of claim 1, further including a pump coupled to said probe assembly to control static pressure within the ear, said computer processor determining said linear response function of the ear as a function of said static pressure.

13. The system of claim 1, further including a pump coupled to said probe assembly to control static pressure within the ear and within said one or more acoustic calibration waveguides, said computer processor determining said linear response function of the ear as a function of said static pressure.

14. The system of claim 1 wherein said electrical input signal has a short duration less than an impulse response duration of said acoustic source.

15. The system of claim 1 wherein said electrical input signal has a duration less than five milliseconds.

16. The system of claim 1 wherein said signal processor receives said set of detected calibration electrical signals and detects therefrom an incident signal in at least one of said one or more acoustic calibration waveguides, said incident signal being separable from a first reflected signal in said at least one acoustic calibration waveguide.

17. The system of claim 16 wherein said first reflected signal results from an acoustic reflection from said second end of said at least one acoustic calibration waveguide.

18. The system of claim 1, further including an allpass filter to process a short duration band-limited signal and thereby generate a time-stretched band-limited signal as said electrical input signal.

19. The system of claim 18 wherein said set of detected calibration electrical energy signals and said detected measurement electrical signal are time-stretched response signals, the system further including an inverse allpass filter to time-compress said time-stretched response signals, whereby said signal processor and said computer processor use said time-compressed set of detected calibration electrical signals and said time-compressed detected measurement electrical signal.

20. The system of claim 19 wherein said signal processor receives said time-compressed set of detected calibration electrical energy signals and detects therefrom an incident signal in at least one of said one or more acoustic calibration waveguides, said incident signal being separable from a first reflected signal in said at least one acoustic calibration waveguide.

21. The system of claim 1 wherein said one or more acoustic calibration waveguides is a single acoustic calibration waveguide and said calibration waveguide model is indicative of an acoustic transfer characteristic, including viscothermal effects, for said single acoustic calibration waveguide, said computer processor determining said linear response function of the ear based on said detected calibration electrical signal from said single acoustic calibration waveguide, said detected measurement electrical signal and said calibration waveguide model.

22. The system of claim 21 wherein said signal processor receives said set of detected calibration electrical signals and detects therefrom an incident signal, said incident signal being separable from a first reflected signal, said computer processor determining said linear response function of the ear using said incident signal and only said first reflected signal as said set of detected calibration electrical signals.

23. The system of claim 21 wherein said predetermined dimensions include an effective length, said signal processor determining said effective length of said single acoustic calibration waveguide by reiteratively calculating a value for said acoustic transfer characteristic as a function of said effective length to minimize the difference between said acoustic transfer characteristic value and an acoustic transfer characteristic model value.

24. The system of claim 21 wherein said signal processor receives said set of detected calibration electrical signals containing an incident signal and a plurality of reflected signals, said incident signal being separable from a first reflected signal, said computer processor determining said linear response function of the ear using said incident signal and said plurality of reflected signals as said set of detected calibration electrical signals.

25. The system of claim 1 wherein said one or more acoustic calibration waveguides comprises a plurality of acoustic calibration waveguides and said signal processor receives said set of detected calibration electrical signals and detects therefrom an incident signal in at least one of said plurality of acoustic calibration waveguides, said incident signal being separable from a first reflected signal in said at least one acoustic calibration waveguide, said computer processor determining said linear response function of the ear based on a weighted average of said set of detected calibration electrical signals from said plurality of acoustic calibration waveguides, said detected measurement electrical signal and said calibration waveguide model.

26. The system of claim 25 wherein said weighted average is an equal weighted average of said set of detected calibration electrical signals from said plurality of acoustic calibration waveguides.

27. The system of claim 25 wherein said computer processor generates a prediction model for each of said plurality of acoustic calibration waveguides based on said calibration waveguide model for each of said plurality of said acoustic calibration waveguides, and said weighted average is proportional to a function of said prediction model for each of said plurality of said acoustic calibration waveguides.

28. The system of claim 25 wherein said weighted average is proportional to a function of said set of detected calibration electrical signals from said plurality of said acoustic calibration waveguides.

29. The system of claim 25 wherein said computer processor generates a prediction model for each of said plurality of acoustic calibration waveguides based on said calibration waveguide model for each of said plurality of said acoustic calibration waveguides, said weighted average being proportional to a function of said prediction model for each of said plurality of said acoustic calibration waveguides and a function of said set of detected calibration electrical signals from said plurality of said acoustic calibration waveguides.

30. The system of claim 25 wherein said set of detected calibration electrical signals from said at least one acoustic calibration waveguide includes said incident signal and only said first reflected signal.

31. The system of claim 25 wherein said signal processor receives said set of detected calibration electrical signals containing said incident signal and a plurality of reflected signals, said incident signal being separable from said first reflected signal in said at least one of said plurality of acoustic calibration waveguides, said computer processor determining said linear response function of the ear using said incident signal and said plurality of reflected signals as said set of detected calibration electrical signals.

32. The system of claim 25 wherein said predetermined dimensions include an effective length and said computer processor generates a prediction model for each of said plurality of acoustic calibration waveguides based on said calibration waveguide model for each of said plurality of said acoustic calibration waveguides, said computer processor determining said effective length of said single acoustic calibration waveguide by reiteratively calculating a value for an acoustic transfer characteristic as a function of said effective length to minimize the difference between said acoustic transfer characteristic value and said prediction model.

33. The system of claim 1 wherein said one or more acoustic calibration waveguides comprises at least two acoustic calibration waveguides, said computer processor determining measurement system parameters using a minimum norm solution of a matrix equation containing matrix elements that are functions of said set of detected calibration electrical signals when said probe assembly is positioned in each of said at least two acoustic calibration waveguides, a prediction model of a predicted linear response for each of said at least two acoustic calibration waveguides based on said calibration waveguide model for each of said at least two acoustic calibration waveguides, and a weighted average of functions of said set of detected calibration electrical signals from said at least two acoustic calibration waveguides and said prediction model for each of said at least two acoustic calibration waveguides, said computer processor determining said linear response function using said detected measurement electrical signal and said measurement system parameters.

34. The system of claim 33 wherein said predetermined dimensions include an effective length, said computer processor determining said effective length of each of said at least two acoustic calibration waveguides by reiteratively calculating a measured linear response as a function of said effective length to minimize a difference between said measured linear response and said prediction model linear response.

35. The system of claim 33 wherein said weighted average is an equal weighted average of said set of detected calibration electrical signals from said at least two acoustic calibration waveguides.

36. The system of claim 33 wherein said weighted average is proportional to a function of said prediction model for each of said at least two acoustic calibration waveguides.

37. The system of claim 33 wherein said weighted average is proportional to a function of said set of detected calibration electrical signals for said at least two acoustic calibration waveguides.

38. The system of claim 33 wherein said computer processor generates said prediction model linear response, said weighted average being proportional to a function of said prediction model linear response for each of said at least two acoustic calibration waveguides and a function of said set of detected calibration electrical signals for said at least two acoustic calibration waveguides.

39. The system of claim 33 wherein said measurement system parameters include an incident field pressure and a source reflectance.

40. The system of claim 33 wherein said measurement system parameters are a Thevenin pressure and a Thevenin source impedance.

41. The system of claim 33 wherein said measurement system parameters are a Norton volume velocity and a Norton source admittance.

42. The system of claim 33 wherein said at least two acoustic calibration waveguides comprises at least three acoustic calibration waveguides, and said matrix equation is an overdetermined matrix equation.

43. The system of claim 33 wherein said minimum norm solution of said matrix equation is a minimum norm solution with regularization.

44. The system of claim 33 wherein said matrix equation is a set of time-domain matrix convolution equations that are solved using pseudoinverse deconvolution.

45. A system for the measurement of a nonlinear power-based transfer function of the ear, the system comprising:
   a probe assembly positionable in the ear;
   an acoustic source within said probe assembly to produce an acoustic stimulus in response to an electrical input signal;
   an acoustic energy detector within said probe assembly to detect acoustic energy signals and convert said detected acoustic energy signals to detected electrical signals;
   a stimulus signal generator coupled to said acoustic source to generate said electrical input signal at first and second stimulus levels to cause said acoustic source to produce acoustic stimuli at first and second acoustic stimulus levels when said probe assembly is positioned in the ear;
   a pump coupled to said probe assembly to control static pressure in the ear;
   a signal processor to receive detected measurement electrical signals in response to said acoustic stimuli at first and second acoustic stimulus levels when said probe assembly is positioned in the ear; and
   a computer processor determining a first power-based transfer function of the ear as a function of said static pressure based on a detected measurement electrical signal in response to said acoustic stimulus at said first acoustic stimulus level and measurement system parameters of said probe assembly, determining a second power-based transfer function of the ear as a function of said static pressure based on a detected measurement electrical signal in response to said acoustic stimulus at said second acoustic stimulus level and measurement system parameters of said probe assembly, said computer processor further determining the power-based nonlinear transfer function based on said first and second transfer functions of the ear and said static pressure.

46. The system of claim 45 wherein said measurement system parameters are a stored calibration model.

47. The system of claim 45 wherein said first and second transfer functions are used to calculate a differential nonlinear transfer function.

48. A system for the measurement of a nonlinear power-based transfer function of the ear, the system comprising:
   one or more acoustic calibration waveguides, each having predetermined dimensions and having first and second ends;
   a probe assembly positionable in the ear;
   an acoustic source within said probe assembly to produce an acoustic stimulus in response to an electrical input signal;
   an acoustic energy detector within said probe assembly to detect acoustic energy signals and convert said detected acoustic energy signals to detected electrical signals;
   a stimulus signal generator coupled to said acoustic source to generate said electrical input signal when said probe assembly is positioned in said first end of said one or more acoustic calibration waveguides, said stimulus signal generator also generating said electrical input signal at first and second stimulus levels to cause said acoustic source to produce acoustic stimuli at first and second acoustic stimulus levels when said probe assembly is positioned in the ear;
   a pump coupled to said probe assembly to control static pressure in the ear;
   a signal processor to receive a set of detected calibration electrical signals from said acoustic energy detector when said probe assembly is positioned in each of said one or more acoustic calibration waveguides and receiving detected measurement electrical signals in response to said acoustic stimuli at first and second acoustic stimulus levels when said probe assembly is positioned in the ear; and
   a computer processor containing a calibration waveguide model indicative of an acoustic transfer characteristic for each of said one or more acoustic calibration waveguides, said computer processor determining first and second power-based transfer functions of the ear as a function of said static pressure based on said detected measurement electrical signals in response to said acoustic stimuli at said first and second acoustic stimulus levels, respectively, said set of detected calibration electrical signals, and said acoustic calibration waveguide model, said computer processor further determining the power-based nonlinear transfer function based on said first and second transfer functions of the ear and said static pressure.

49. The system of claim 48 wherein said model is a stored response of said probe assembly.

50. The system of claim 48 wherein said model is a predictive model of said acoustic transfer characteristic.

51. The system of claim 48 wherein said first and second transfer functions are used to calculate a differential nonlinear transfer function.

52. A system for the measurement of a power absorbed by the ear, the system comprising:
   a probe assembly positionable in the ear;
   an acoustic source within said probe assembly to produce an acoustic stimulus in response to an electrical input signal;
   an acoustic energy detector within said probe assembly to detect acoustic energy signals and convert said detected acoustic energy signals to detected electrical signals;
   a stimulus signal generator coupled to said acoustic source to generate said electrical input signal at first and second stimulus levels to cause said acoustic source to produce acoustic stimuli at first and second acoustic stimulus levels when said probe assembly is positioned in the ear;
   a signal processor to receive detected measurement electrical signals in response to said acoustic stimuli at first and second acoustic stimulus levels when said probe assembly is positioned in the ear; and
   a computer processor determining a first power-based transfer function of the ear based on a first detected measurement electrical signal in response to said acoustic stimulus at said first acoustic stimulus level, determining a second power-based transfer function of the ear based on a second detected measurement electrical signal in response to said acoustic stimulus at said second acoustic stimulus level, said computer processor further determining the power absorbed by the ear at said first and second acoustic stimuli levels based on said first and second transfer functions and said first and second detected measurement electrical signals.

53. The system of claim 52, further including one or more acoustic calibration waveguides, each having predetermined dimensions and having first and second ends and a calibration waveguide model indicative of an acoustic transfer characteristic for each of said one or more acoustic calibration waveguides, said stimulus signal generator also generating said electrical input signal when said probe assembly is positioned in said first end of said one or more acoustic calibration waveguides, said signal processor also receiving a set of detected calibration electrical signals from said acoustic energy detector when said probe assembly is positioned in each of said one or more acoustic calibration waveguides, said computer processor determining measurement system parameters based on said set of detected calibration electrical signals and said calibration waveguide model, said computer processor further determining said first and second transfer functions of the ear based on said detected measurement electrical signals in response to said acoustic stimuli at said first and second acoustic stimulus levels, respectively, said set of detected calibration electrical signals, and said acoustic calibration waveguide model.

54. The system of claim 52 wherein said probe assembly is characterized by measurement system parameters in a stored calibration model.

55. The system of claim 52 wherein said probe assembly is characterized by measurement system parameters including a predictive model of said measurement system parameters.

56. The system of claim 52 wherein said computer processor calculates a differential nonlinear power absorbed by the ear.

57. The system of claim 52, further including a pump coupled to said probe assembly to control static pressure in the ear, said computer processor determining said first and second transfer functions of the ear and said power absorbed by the ear as a function of said static pressure.

58. A system for the measurement of a nonlinear power-based transfer function of the ear, the system comprising:

a probe assembly positionable in the ear;

an acoustic source within said probe assembly to produce an acoustic stimulus in response to an electrical input signal;

an acoustic energy detector within said probe assembly to detect acoustic energy signals and convert said detected acoustic energy signals to detected electrical signals;

one or more acoustic calibration waveguides, each having predetermined dimensions and having first and second ends;

a stimulus signal generator coupled to said acoustic source to generate said electrical input signal when said probe assembly is positioned in said first end of said one or more acoustic calibration waveguides, said stimulus signal generator also generating said electrical input signal at first and second stimulus levels to cause said acoustic source to produce acoustic stimuli at first and second acoustic stimulus levels when said probe assembly is positioned in the ear;

a signal processor to receive a set of detected calibration electrical signals from said acoustic energy detector when said probe assembly is positioned in each of said one or more acoustic calibration waveguides and to receive detected measurement electrical signals in response to said acoustic stimuli at first and second acoustic stimulus levels when said probe assembly is positioned in the ear; and a computer processor containing a calibration waveguide model indicative of an acoustic transfer characteristic, including viscothermal effects, for each of said one or more acoustic calibration waveguides, said computer processor determining a first power-based transfer function of the ear based on said set of detected calibration electrical signals, said detected measurement electrical signals in response to said acoustic stimulus at said first acoustic stimulus level, and said calibration waveguide model, determining a second power-based transfer function of the ear based on said set of detected calibration electrical signals, said detected measurement electrical signals in response to said acoustic stimulus at said second acoustic stimulus level, and said calibration waveguide model, said computer processor further determining the power-based nonlinear transfer function based on said first and second transfer functions.

59. The system of claim 58, further including a pump coupled to said probe assembly to control static pressure within the ear, said computer processor determining said first and second transfer functions of the ear as functions of said static pressure.

60. The system of claim 58 wherein said signal processor receives said set of detected calibration electrical signals and detects therefrom an incident signal in at least one of said one or more acoustic calibration waveguides, said incident signal being separable from a first reflected signal in said at least one acoustic calibration waveguide.

61. The system of claim 60 wherein said first reflected signal results from an acoustic reflection from said second end of said one or more acoustic calibration waveguides.

62. The system of claim 58, further including an allpass filter to process a short duration band-limited signal and thereby generate a time-stretched band-limited signal as said electrical input signal.

63. The system of claim 62 wherein said set of detected calibration electrical energy signals and said detected measurement electrical signals are time-stretched response signals, the system further including an inverse allpass filter to time-compress said time-stretched response signals, whereby said signal processor and said computer processor use said time-compressed set of calibration electrical signals and said time-compressed measurement electrical signals.

64. The system of claim 63 wherein said signal processor receives said time-compressed set of detected calibration electrical energy signals and detects therefrom an incident signal in at least one of said one or more acoustic calibration waveguides, said incident signal being separable from a first reflected signal in said at least one acoustic calibration waveguide.

65. The system of claim 58 wherein said stimulus signal generator generates said electrical input signal at said first and second stimulus levels to cause said acoustic source to produce acoustic stimuli at said first and second acoustic stimulus levels when said probe assembly is positioned in said first end of each of said one or more acoustic calibration waveguides, said set of detected calibration electrical signals including detected calibration electrical signals in response to said acoustic stimuli at said first and second acoustic stimulus levels when said probe assembly is positioned in said first end of each of said one or more acoustic calibration waveguides.

66. The system of claim 58 wherein said stimulus signal generator generates said electrical input signal at said first stimulus level to cause said acoustic source to produce an acoustic stimulus at said first acoustic stimulus level when said probe assembly is positioned in said first end of each of said one or more acoustic calibration waveguides, said set of detected calibration electrical signals including detected calibration electrical signals in response to said acoustic stimulus at said first acoustic stimulus level when said probe assembly is positioned in said first end of each of said one or more acoustic calibration waveguides.

67. The system of claim 58 wherein said one or more acoustic calibration waveguides is a single acoustic calibration waveguide and said calibration waveguide model is indicative of an acoustic transfer characteristic, including viscothermal effects, for said single acoustic calibration waveguide, said computer processor determining said first and second transfer functions of the ear based on said set of detected calibration electrical signals, said detected measurement electrical signals in response to said acoustic stimuli at first and second acoustic stimulus levels, respectively, when said probe assembly is positioned in the ear, and said calibration waveguide model.

68. The system of claim 67 wherein said signal processor receives said set of detected calibration electrical signals and detects therefrom an incident signal, said incident signal being separable from a first reflected signal, said computer processor determining said first and second transfer functions of the ear using said incident signal and only said first reflected signal as said set of detected calibration electrical signals.

69. The system of claim 67 wherein said predetermined dimensions include an effective length, said signal processor determining said effective length of said single acoustic calibration waveguide by reiteratively calculating a value for said acoustic transfer characteristic as a function of said effective length to minimize the difference between said acoustic transfer characteristic value and an acoustic transfer characteristic model value.

70. The system of claim 67 wherein said signal processor receives said set of detected calibration electrical signals containing an incident signal and a plurality of reflected signals, said incident signal being separable from a first reflected signal, said computer processor determining said first and second transfer functions of the ear using said incident signal and said plurality of reflected signals as said set of detected calibration electrical signals.

71. The system of claim 58 wherein said one or more acoustic calibration waveguides comprises a plurality of acoustic calibration waveguides and said signal processor receives said set of detected calibration electrical signals and detects therefrom an incident signal in at least one of said plurality of acoustic calibration waveguides, said incident signal being separable from a first reflected signal in said at least one acoustic calibration waveguide, said computer processor determining said first and second transfer functions of the ear based on a weighted average of said set of detected calibration electrical signals from said plurality of acoustic calibration waveguides, said detected measurement electrical signals in response to said acoustic stimuli at first and second acoustic stimulus levels, respectively, when said probe assembly is positioned in the ear, and said calibration waveguide model.

72. The system of claim 58 wherein said one or more acoustic calibration waveguides comprises at least two acoustic calibration waveguides, said computer processor determining measurement system parameters using a minimum norm solution of a matrix equation containing matrix elements that are functions of said set of detected calibration electrical signals when said probe assembly is positioned in each of said at least two acoustic calibration waveguides, a prediction model of a predicted linear response for each of said at least two acoustic calibration waveguides based on said calibration waveguide model for each of said at least two acoustic calibration waveguides, and a weighted average of functions of said set of detected calibration electrical signals from said at least two acoustic calibration waveguides, said computer processor determining said first and second transfer functions of the ear using said detected measurement electrical signals in response to said acoustic stimuli at said first and second acoustic stimulus levels, respectively, when said probe assembly is positioned in the ear, and said measurement systems parameters.

73. The system of claim 72 wherein said stimulus signal generator generates said electrical input signal at said first and second stimulus levels to cause said acoustic source to produce acoustic stimuli at said first and second acoustic stimulus levels when said probe assembly is positioned in said first end of each of said at least two acoustic calibration waveguides, said set of detected calibration electrical signals including detected electrical signals in response to said acoustic stimuli at said first and second acoustic stimulus levels when said probe assembly is positioned in said first end of each of said at least two acoustic calibration waveguides.

74. The system of claim 72 wherein said stimulus signal generator generates said electrical input signal at said first stimulus level to cause said acoustic source to produce an acoustic stimulus at said first acoustic stimulus level when said probe assembly is positioned in said first end of each of said at least two acoustic calibration waveguides, said set of detected calibration electrical signals including detected electrical signals in response to said acoustic stimuli at said first acoustic stimulus level when said probe assembly is positioned in said first end of each of said at least two acoustic calibration waveguides.

75. The system of claim 58 wherein said first and second transfer functions are used to calculate a differential nonlinear transfer function.

76. The system of claim 58 wherein said computer processor calculates power absorbed by the ear as a function of stimulus level.

77. The system of claim 58 wherein said computer processor calculates a differential nonlinear power absorbed by the ear.

78. A system for the measurement of a reflectance of the ear, the system comprising:

a probe assembly positionable in the ear;

an acoustic source within said probe assembly to produce an acoustic stimulus in response to an electrical input signal;

an acoustic energy detector within said probe assembly to detect acoustic energy signals and convert said detected acoustic energy signals to detected electrical signals;

a stimulus signal generator coupled to said acoustic source to generate said electrical input signal when said probe assembly is positioned in the ear;

a pump coupled to said probe assembly to control static pressure in the ear;

a signal processor receiving a detected electrical signal when said probe assembly is positioned in the ear, said signal processor calculating a transfer function of the ear as a function of said static pressure;

a storage area containing an estimate of an ear canal area; and a computer processor receiving said transfer function and said ear canal estimate from said storage area, said computer processor calculating the reflectance of the ear as a function of said static pressure.

79. The system of claim 78 wherein said signal processor is a portion of a tympanometer.

80. The system of claim 79 wherein said transfer function calculated by said signal processor is an admittance.

81. The system of claim 78 wherein said stimulus generator generates a signal at a selected frequency, said signal processor also calculating said transfer function of the ear as a function of said selected frequency, said computer processor calculating said reflectance of the ear as a function of said static pressure and said selected frequency.

82. A method for the measurement of a linear response of the ear, the method comprising the steps of:

positioning a probe assembly in one or more acoustic calibration waveguides, each having predetermined dimensions and having first and second ends;

generating an electrical input signal to an acoustic source within said probe assembly when said probe assembly is positioned in said first end of said one or more acoustic calibration waveguides to produce an acoustic stimulus in response to said electrical input signal;

detecting acoustic energy signals with an acoustic energy detector within said probe assembly and converting said detected acoustic energy signals to detected electrical signals;

receiving a set of detected calibration electrical signals from said acoustic energy detector when said probe assembly is positioned in each of said one or more acoustic calibration waveguides;

positioning said probe assembly in the ear;

generating said electrical input signal when said probe assembly is positioned in the ear;

receiving a detected measurement electrical signal when said probe assembly is positioned in the ear; and determining a linear response function of the ear based on said set of detected calibration electrical signals and detected measurement electrical signal and a calibration waveguide model indicative of an acoustic transfer characteristic, including viscothermal effects, for each of said one or more acoustic calibration waveguides.

83. The method of claim 82 wherein said linear response function of the ear includes a time-domain linear response function of the ear.

84. The method of claim 83 wherein said time-domain linear response function comprises a selected one of a set including a reflection function, a time-domain impedance function and a time-domain admittance function.

85. The method of claim 82 wherein said linear response function of the ear includes a frequency-domain linear response function of the ear.

86. The method of claim 85 wherein said frequency-domain linear response function comprises a selected one of a set including a reflection coefficient function, an impedance function, and an admittance function.

87. The method of claim 82 wherein said predetermined dimensions include an acoustic calibration waveguide length and a cross-sectional area as a function of position along said acoustic calibration waveguide for each of said one or more acoustic calibration waveguides.

88. The method of claim 87 wherein each of said one or more acoustic calibration waveguides is a cylindrical tube with said cross-sectional area having a constant value as a function of said position.

89. The method of claim 82 wherein said second end in each of said one or more acoustic calibration waveguides is terminated by an acoustic termination having known acoustic transfer characteristics to define said calibration waveguide model.

90. The method of claim 82, further including the step of controlling static pressure within the ear, said step of determining said linear response function determining said linear response function of the ear as a function of said static pressure.

91. The method of claim 82, further including the step of controlling static pressure within the ear and within said one or more acoustic calibration waveguides, said step of determining said linear response function determining said linear response function of the ear as a function of said static pressure.

92. The method of claim 82 wherein said steps of generating said electrical input signal uses a signal having a short duration less than an impulse response duration of said acoustic source.

93. The method of claim 82 wherein said electrical input signal has a duration less than five milliseconds.

94. The method of claim 82, further including the step of detecting, from said detected calibration electrical signals detected when said probe assembly is positioned in at least one of said one or more acoustic calibration waveguides, an incident signal, said incident signal being separable from a first reflected signal in said at least one acoustic calibration waveguide.

95. The method of claim 94 wherein said first reflected signal results from an acoustic reflection from said second end of said at least one acoustic calibration waveguide.

96. The method of claim 82, further including the step of allpass filtering a short duration band-limited signal and thereby generating a time-stretched band-limited signal as said electrical input signal.

97. The method of claim 96 wherein said set of detected calibration electrical energy signals and said detected measurement electrical energy signal are time-stretched response signals, the method further including the steps of inverse allpass filtering said time-stretched response signals to time-compress said time-stretched response signals, wherein said step of determining said linear response function of the ear is based on said time-compressed set of detected calibration electrical signals and said time-compressed measurement electrical signal.

98. The method of claim 97, further including the step of detecting, from said time-compressed set of detected calibration electrical energy signals when said probe assembly is positioned in at least one of said one or more acoustic calibration waveguides, an incident signal, said incident signal being separable from a first reflected signal in said at least one acoustic calibration waveguide.

99. The method of claim 82 wherein said one or more acoustic calibration waveguides is a single acoustic calibration waveguide and said calibration waveguide model is indicative of an acoustic transfer characteristic, including viscothermal effects, for said single acoustic calibration waveguide, said step of determining said linear response function of the ear based using said detected calibration electrical signal from said single acoustic calibration waveguide, said detected measurement electrical signal and said calibration waveguide model.

100. The method of claim 99 wherein said step of receiving said set of detected calibration electrical signals includes the step of detecting therefrom an incident signal, said incident signal being separable from a first reflected signal, said step of determining said linear response function of the ear using said incident signal and only said first reflected signal as said set of detected calibration electrical signals.

101. The method of claim 99 wherein said predetermined dimensions include an effective length, the method further including the step of determining said effective length of said single acoustic calibration waveguide by reiteratively calculating a value for said acoustic transfer characteristic as a function of said effective length to minimize the difference between said acoustic transfer characteristic value and an acoustic transfer characteristic model value.

102. The method of claim 99 wherein said set of detected calibration electrical signals contains an incident signal and a plurality of reflected signals, said incident signal being separable from a first reflected signal, said step of determining said linear response function of the ear using said incident signal and said plurality of reflected signals as said set of detected calibration electrical signals.

103. The method of claim 82 wherein said one or more acoustic calibration waveguides comprises a plurality of acoustic calibration waveguides and said step of receiving said set of detected calibration electrical signals includes the step of detecting therefrom an incident signal in at least one of said plurality of acoustic calibration waveguides, said incident signal being separable from a first reflected signal in said at least one acoustic calibration waveguide, said step of determining said linear response function of the ear based on a weighted average of said set of detected calibration electrical signals from said plurality of acoustic calibration waveguides, said detected measurement electrical signal and said calibration waveguide model.

104. The method of claim 103 wherein said set of detected calibration electrical signals from said at least one acoustic calibration waveguide includes said incident signal and only said first reflected signal.

105. The method of claim 103 wherein said signal processor receives said set of detected calibration electrical signals includes said incident signal and a plurality of reflected signals, said incident signal being separable from said first reflected signal in said at least one of said plurality of acoustic calibration waveguides, said step of determining said linear response function of the ear using said incident signal and said plurality of reflected signals as said set of detected calibration electrical signals.

106. The method of claim 82 wherein said one or more acoustic calibration waveguides comprises at least two acoustic calibration waveguides, said step of determining said linear response measurement also determining measurement system parameters using a minimum norm solution of a matrix equation containing matrix elements that are functions of said set of detected calibration electrical signals when said probe assembly is positioned in each of said at least two acoustic calibration waveguides, a prediction model of a predicted linear response for each of said at least two acoustic calibration waveguides based on said calibration waveguide model for each of said at least two acoustic calibration waveguides, and a weighted average of functions of said set of detected calibration electrical signals from said at least two acoustic calibration waveguides, said step of determining said linear response function using said detected measurement electrical signal and said measurement system parameters.

107. A method for the measurement of a nonlinear power-based transfer function of the ear, the method comprising the steps of:

positioning a probe assembly in one or more acoustic calibration waveguides, each having predetermined dimensions and first and second ends;

generating electrical input signals for an acoustic source within said probe assembly when said probe assembly is positioned in said first end of said one or more acoustic calibration waveguides to produce acoustic stimuli in response to said electrical input signals;

detecting acoustic energy signals with an acoustic energy detector within said probe assembly and converting said detected acoustic energy signals to detected calibration electrical signals;

receiving said set of detected calibration electrical signals from said acoustic energy detector when said probe assembly is positioned in each of said one or more acoustic calibration waveguides;

positioning said probe assembly in the ear;

generating said electrical input signal at first and second levels to cause said acoustic source to produce acoustic stimuli at first and second acoustic stimulus levels, respectively, when said probe assembly is positioned in the ear;

receiving first and second detected measurement electrical signals in response to said acoustic stimuli at first and second acoustic stimulus levels, respectively, when said probe assembly is positioned in the ear;

determining a first power-based transfer function of the ear based on said set of detected calibration electrical signals in said one or more acoustic calibration waveguides, said first detected measurement electrical signal, and a calibration waveguide model indicative of an acoustic transfer characteristic, including viscothermal effects, for each of said one or more acoustic calibration waveguides;

determining a second power-based transfer function of the ear based on said set of detected calibration electrical signals in said one or more acoustic calibration waveguides, said second detected measurement electrical signal, and said calibration waveguide model; and determining the nonlinear power-based transfer function of the ear based on said first and second transfer functions.

108. A method for the measurement of a nonlinear power-based transfer function of the ear, the system comprising:

positioning a probe assembly in the ear;

generating an electrical input signal at first and second stimulus levels to produce acoustic stimuli at first and second acoustic stimulus levels when said probe assembly is positioned in the ear;

varying static pressure in the ear in a controlled fashion;

receiving first and second detected measurement electrical signals in response to said acoustic stimuli at first and second acoustic stimulus levels, respectively, when said probe assembly is positioned in the ear;

determining a first power-based transfer function of the ear of the ear as a function of said static pressure based on said first detected measurement electrical signal and measurement system parameters of said probe assembly;

determining a second power-based transfer function of the ear of the ear as a function of said static pressure based on said second detected measurement electrical signal and said measurement system parameters; and determining the power-based nonlinear transfer function based on said first and second transfer functions of the ear and said static pressure.

109. A method for the measurement of a nonlinear power-based transfer function of the ear, the method comprising the steps of:

positioning a probe assembly in one or more acoustic calibration waveguides, each having predetermined dimensions and first and second ends;

generating electrical input signals for an acoustic source within said probe assembly when said probe assembly is positioned in said first end of said one or more acoustic calibration waveguides to produce acoustic stimuli in response to said electrical input signals;

detecting acoustic energy signals with an acoustic energy detector within said probe assembly and converting said detected acoustic energy signals to detected calibration electrical signals;

receiving said set of detected calibration electrical signals from said acoustic energy detector when said probe assembly is positioned in each of said one or more acoustic calibration waveguides;

positioning a probe assembly in the ear;

varying static pressure in the ear in a controlled fashion;

generating said electrical input signal at first and second levels to cause said acoustic source to produce acoustic stimuli at first and second acoustic stimulus levels, respectively, when said probe assembly is positioned in the ear;

receiving detected measurement electrical signals in response to said acoustic stimuli at first and second acoustic stimulus levels when said probe assembly is positioned in the ear;

determining a first power-based transfer function of the ear as a function of said static pressure based on said set of detected calibration electrical signals in said one or more acoustic calibration waveguides, said detected measurement electrical signals in response to said acoustic stimulus at said first acoustic stimulus level, and a calibration waveguide model indicative of an acoustic transfer characteristic for each of said one or more acoustic calibration waveguides;

determining a second power-based transfer function of the ear as a function of said static pressure based on said set of detected calibration electrical signals in said one or more acoustic calibration waveguides, said detected measurement electrical signals in response to said acoustic stimulus at said second acoustic stimulus level, and said calibration waveguide model for each of said one or more acoustic calibration waveguides; and determining the nonlinear power-based transfer function of the ear based on said first and second transfer functions and said static pressure.

110. A method for the measurement of a power absorbed by the ear, the method comprising the steps of:

positioning a probe assembly in the ear;

generating an electrical input signal at first and second levels to cause an acoustic source within said probe assembly to produce acoustic stimuli at first and second acoustic stimulus levels, respectively, when said probe assembly is positioned in the ear;

detecting acoustic energy signals and converting said detected acoustic energy signals to detected electrical signals;

receiving first and second detected measurement electrical signals in response to said acoustic stimuli at first and second acoustic stimulus levels, respectively, when said probe assembly is positioned in the ear;

determining a first power-based transfer function of the ear based on said first detected measurement electrical signal;

determining a second power-based transfer function of the ear based on said second detected measurement electrical signal; and determining the power absorbed by the ear at said first and second acoustic stimuli levels based on said first and second transfer functions and said first and second detected measurement electrical signals.

111. The method of claim 110, further including the steps of positioning said probe assembly in one or more acoustic calibration waveguides, each having predetermined dimensions and having first and second ends, generating said electrical input signal when said probe assembly is positioned in said first end of said one or more acoustic calibration waveguides, detecting a set of detected calibration electrical signals from said acoustic energy detector when said probe assembly is positioned in each of said one or more acoustic calibration waveguides, said step of determining said first and second power-based transfer functions of the ear determining said first and second power-based transfer functions based on said first and second detected measurement electrical signals, respectively, said set of detected calibration electrical signals and a calibration waveguide model indicative of an acoustic transfer function of said one or more acoustic calibration waveguides.

112. The method of claim 110, further including the step of varying static pressure in the ear in a controlled manner, said steps of determining said first and second transfer functions of the ear and said power absorbed by the ear determining said first and second transfer functions of the ear and said power absorbed by the ear as a function of said static pressure.

113. A method for the measurement of a reflectance of the ear, the system comprising:

positioning a probe assembly in the ear;

generating an electrical input signal to an acoustic source within said probe assembly to produce an acoustic stimulus in response to said electrical input signal;

receiving a detected measurement electrical signal when said probe assembly is positioned in the ear;

varying static pressure in the ear in a controlled fashion;

calculating a transfer function of the ear as a function of said static pressure;

estimating an ear canal area; and receiving said transfer function and said ear canal area estimate and calculating therefrom the reflectance of the ear as a function of said static pressure.

114. The method of claim 113 wherein said step of calculating said transfer function of the ear is performed by a tympanometer.

115. The method of claim 114 wherein said transfer function calculated by said tympanometer is an admittance.

116. The method of claim 113 wherein said step of generating said generating said electrical input signal to said acoustic source generates a signal at a selected frequency, and said step of calculating said response function of the ear as a function of said static pressure also calculates said response function of the ear as a function of said selected frequency, said step of calculating said reflectance of the ear as a function of said static pressure calculating said reflectance of the ear as a function of said static pressure and said selected frequency.

* * * * *